(12) United States Patent
Shamay et al.

(10) Patent No.: US 11,179,170 B2
(45) Date of Patent: Nov. 23, 2021

(54) SYSTEMS FOR THROMBECTOMY

(71) Applicant: AMNIS THERAPEUTICS LTD, Or Akiva (IL)

(72) Inventors: Noam Shamay, Elyachin (IL); Ronen Ariel Plis, Maor (IL); Shahar Cohen, Kiryat Bialik (IL)

(73) Assignee: AMNIS THERAPEUTICS LTD, Or Akiva (IL)

( * ) Notice: Subject to any disclaimer, the term of this patent is extended or adjusted under 35 U.S.C. 154(b) by 285 days.

(21) Appl. No.: 15/770,943

(22) PCT Filed: Oct. 26, 2016

(86) PCT No.: PCT/IL2016/051153
§ 371 (c)(1),
(2) Date: Apr. 25, 2018

(87) PCT Pub. No.: WO2017/072761
PCT Pub. Date: May 4, 2017

(65) Prior Publication Data
US 2018/0325537 A1    Nov. 15, 2018

Related U.S. Application Data

(60) Provisional application No. 62/246,139, filed on Oct. 26, 2015, provisional application No. 62/257,346, filed on Nov. 19, 2015.

(51) Int. Cl.
*A61B 17/221* (2006.01)
*A61B 17/22* (2006.01)

(52) U.S. Cl.
CPC .... *A61B 17/221* (2013.01); *A61B 2017/2215* (2013.01); *A61B 2017/22034* (2013.01)

(58) Field of Classification Search
CPC ............ A61B 17/221; A61B 17/22031; A61B 2017/22034; A61B 2017/2217; A61B 2017/2215
See application file for complete search history.

(56) References Cited

U.S. PATENT DOCUMENTS

| 6,685,722 B1 | 2/2004 | Rosenbluth et al. |
| 7,766,921 B2 | 8/2010 | Sepetka et al. |

(Continued)

FOREIGN PATENT DOCUMENTS

| CN | 2848137 Y | 12/2006 |
| CN | 101340849 A | 1/2009 |

(Continued)

OTHER PUBLICATIONS

Gory et al., "Histopathologic Evaluation of Arterial Wall Response to 5 Neurovascular Mechanical Thrombectomy Devices in a Swine Model", Am J Neuroradiol, vol. 34, pp. 2192-2198, (2013).

(Continued)

*Primary Examiner* — Katherine M Rodjom
(74) *Attorney, Agent, or Firm* — Vorys, Sater, Seymour & Pease LLP; William Klima

(57) ABSTRACT

Provided are medical systems, kits and methods for retrieval and/or extraction of a corpus located in a tubular organ. Further provided are systems configured for carrying out various procedures for removal of occlusive corpus from tubular organs, for example thrombectomy.

20 Claims, 25 Drawing Sheets

(56) References Cited

U.S. PATENT DOCUMENTS

| | | |
|---|---|---|
| 8,715,227 B2 | 5/2014 | Kontos |
| 8,814,892 B2 | 8/2014 | Galdonik et al. |
| 2005/0049619 A1 | 3/2005 | Sepetka et al. |
| 2005/0283186 A1 | 12/2005 | Berrada et al. |
| 2007/0162048 A1 | 7/2007 | Quinn et al. |
| 2010/0023035 A1* | 1/2010 | Kontos .......... A61B 17/320725 606/159 |
| 2011/0251629 A1* | 10/2011 | Galdonik ............. A61B 17/221 606/159 |
| 2014/0222062 A1* | 8/2014 | Shamay ............... A61B 17/064 606/200 |
| 2014/0309657 A1 | 10/2014 | Ben-Ami |
| 2014/0371779 A1 | 12/2014 | Vale et al. |
| 2015/0018860 A1 | 1/2015 | Quick et al. |

FOREIGN PATENT DOCUMENTS

| | | |
|---|---|---|
| JP | 2013-542758 A | 11/2013 |
| SU | 1597180 A1 | 10/1990 |
| WO | 2009/086482 A1 | 7/2009 |
| WO | 2011/130256 A2 | 10/2011 |
| WO | 2013/054324 A1 | 4/2013 |
| WO | 2015/061365 A1 | 4/2015 |

OTHER PUBLICATIONS

Gralla et al., "A Dedicated Animal Model for Mechanical Thrombectomy in Acute Stroke", Am J Neuroradiol, vol. 27, pp. 1357-1361, (2006).

Grunwald et al., "Endovascular Stroke Treatment Today", The American Journal of Neuroradiology, vol. 32, pp. 238-243, (2011).

Levy et al., "Self-Expanding Versus Balloon-Mounted Stents for Vessel Recanalization Following Embolic Occlusion in the Canine Model: Technical Feasibility Study", Am J Neuroradiol, vol. 27, pp. 2069-2072, (2006).

Mordasini et al., "Thrombectomy for Acute Ischemic Stroke Treatment: A Review", The eJournal of the European Society of Minimally Invasive Neurological Therapy, 1238000077, 10 pages, (2012).

Nogueira et al., "Endovascular Approaches to Acute Stroke, Part 1: Drugs, Devices, and Data", AJNR Am J Neuroradiol, vol. 30, pp. 649-661, (2009).

* cited by examiner

SYSTEMS FOR THROMBECTOMY

TECHNOLOGICAL FIELD

The present disclosure relates to anchoring and retrieval of a corpus in an organ of a subject, in particular narrow tubular organs such as small blood vessels.

BACKGROUND ART

References considered to be relevant as background to the presently disclosed subject matter are listed below:
[1] Nogueira et al., *AJNR* 2009, 30, 649-661
[2] Grunwald et al. *The American Journal of Neuroradiology* 2011, 32, 238-243
[3] Mordasini et al. *The eJournal of the European Society of minimally invasive Neurological Therapy*, 2012: 1238000077
[4] U.S. Pat. No. 7,766,921
[5] U.S. Pat. No. 8,715,227
[6] U.S. Pat. No. 6,685,722
[7] WO 2013/054324
[8] Gralla et al., *Am J Neuroradiol* 2006, 27, 1357-1361
[9] WO 2011/130256
[10] Gory et al., *Am J Neuroradiol* 2013, 34, 2192-2198
[11] Levy et al., *Am J Neuroradiol* 2006, 27, 2069-2072

Acknowledgement of the above references herein is not to be inferred as meaning that these are in any way relevant to the patentability of the presently disclosed subject matter.

BACKGROUND

The removal of blood clots and plaque from blood vessels by use of minimally invasive procedures is nowadays a well-established practice. A stroke event associated with a blood clot occurs as a result of disturbance in the blood vessels supplying blood to the brain, leading to sudden death of brain cells. This can be due to ischemia (lack of glucose and oxygen supply) caused by thrombosis (~80% of strokes) or due to a hemorrhage (~20% of strokes). The annual prevalence of stroke is estimated to be 15 million people worldwide and it is one of the leading causes of death (~10% of all deaths) and long-term disability. Furthermore, stroke is one of the most costly health problems in America and the Western world, with estimated direct and indirect costs of $38.6 billion annually. The majority of the damage caused by a stroke is due to secondary stroke damage which threatens the functionally of the impaired region that surrounds the infarct core; the ischemic penumbra. Early medical intervention (for re-canalization) can inhibit this process and reduce the risk for irreversible neurological damage.

The goal of treatment for stroke resulting from thrombus remains the same: safe and rapid re-establishment of oxygenated blood flow to the affected tissue. Guidelines and protocols for the treatment of ischemic stroke are, for example, those published by the American Society of Neurology and the American Society of Neurosurgeons or The European Stroke Organization (ESO). More specifically, the pharmacologic standard of care for ischemic stroke patients to date is by intravenous (IV) tissue plasminogen activator (rt-PA). Improvement in re-canalization rate may be achieved when rt-PA is used intra-arterially (IA) within 6 hours of symptom onset, in patients with occlusions in a large-vessel (e.g., middle cerebral artery), or patients who have contraindications for the use of IV thrombolysis. However, this treatment may increase the risk for intracranial hemorrhage and is currently not approved for use worldwide. Beyond the failure rates of thrombolytic therapy, it is also limited in the time window for treatment and indicated population. Therefore, in patients who have either failed IV rt-PA therapy or who are either ineligible for or have contraindications to IV rt-PA use, or are out of the therapeutic window when medical support can be initiated, neurothrombectomy devices have been used for the re-establishment of blood flow.

Various mechanical approaches to fragment or retrieve clots have been utilized and reported in the clinical literature. These include, inter alia, endovascular (intracranial) thrombectomy, endovascular thromboaspiration, mechanical thrombus disruption and thrombus entrapment devices [1-6]. Intracranial thrombectomy may provide rapid flow restoration with a potentially lower likelihood of clot fragmentation and distal embolism, lessens and even preclude the use of chemical thrombolytics—thus reducing the risk of neurotoxicity and intracranial hemorrhage. By avoiding the use of chemical thrombolytics, it could be possible to extend the treatment window to 8 hours and beyond. In addition, re-canalization occurs without the disruption of the blood-brain-barrier. For example, some systems are based on deployment of devices in a collapsed state, that are expanded for retrieval of the blood clot once inserted into the blood vessel [4]. Others comprise a plurality of strands, and have contracted and expanded configurations [5-7, 9].

Due to the variability in the properties of blood clots, many of the devices described in the art are suitable for extraction of a specific type of clots. Moreover, in most cases the devices are designed to provide support for the artery as well as function to provide embolic protection, thereby necessitating direct contact with the internal face of the blood vessel. Such contact often causes additional damage to the blood vessel when the device is manipulated and moved within the vessel during the different stages of the procedure. Thus, there is a need for a device allowing extraction of various clots from a variety of blood vessels, reducing the risk of clot disintegration, while providing greater operational flexibility and minimal blood vessel damage.

GENERAL DESCRIPTION

The present disclosure relates to a medical system, kits and methods for retrieval and/or extraction of a corpus located in a tubular organ. Thus, the system of this disclosure is suitable for carrying out various procedures for removal of occlusive corpus from tubular organs. An exemplary procedure may be thrombectomy (i.e. removal of blood clots), typically in narrow blood vessels such as, but not limited to, those existing in the brain, by anchoring the device into the corpus in a manner permitting its extraction from the blood vessel without significant fracturing of the corpus or without significantly damaging the blood vessel.

In the context of the present disclosure, the term corpus encompasses blood clots, plaque, cholesterol layers, thrombus, naturally-occurring foreign bodies (e.g. tissue portions trapped within or adhered to the inner face of the tubular organ), non naturally-occurring foreign bodies (e.g. non-biological objects trapped within, adhered to or penetrating through the tubular organ), and the like.

The term tubular organ means to encompass any anatomical lumen of a subject to be treated that enables flow of a bodily-fluid therethrough. The organ may be a blood vessel (a vain, an artery, micro blood vessels, etc.), or a non-vascular anatomical organ, such as fallopian tubes, urinary tract (e.g. ureter, urethra, kidneys), biliary tract (bile ducts), gastrointestinal tract, airways and any other anatomical lumen in which partial or full blockage may occur.

In one of its aspects this disclosure provides a medical system for anchoring into at least one corpus located in a tubular organ, the system comprising a handling and manipulation apparatus (HMA) and a corpus anchoring unit operable thereby. The HMA is configured for manipulating the corpus anchoring unit into engagement with the corpus, and once in proximity to the corpus the anchoring unit is manipulated into operation by the HMA.

The corpus anchoring unit comprises a deployment wire defining a proximal-distal axis, at least two generally cylindrical elongated bodies that are spaced apart along said deployment wire, and at least two axially displaceable tip tools. Each cylindrical body is constituted by at least one, typically a plurality of, wound coiled threads that form the cylindrical structure of the cylindrical body; each such cylindrical body has a proximal end and a distal end. The at least one wound coiled thread (and hence also the cylindrical body) has a deployment state, in which it is coiled and wound to form the cylindrical shape of the cylindrical body (i.e. forming the general shape of a tube)—each of said cylindrical bodies having a fixed end at either the proximal or distal end. The coiled wound threads are held at the cylindrical body's fixed end one against the other, to prevent the threads' deployment at the fixed end. The opposite end of the cylindrical body is a free end, that is configured for deploying the wound coiled threads (and hence also the cylindrical body) from their deployment state into at least one deployed state. In the deployed state, each of the threads unwinds in the general radial direction while tracing, during deployment, a generally helical path. Thus, during deployment, the free end of each of the unwinding coiled threads moves in a general screw-like movement, thereby anchoring the unwound threads into the corpus.

A tip tool (of said at least two axially displaceable tip tools) is located such that it is associated with one of the proximal or distal ends of the tip's corresponding cylindrical body. Namely, each cylindrical body has an associated tip tool, which is associated either with the proximal end or with the distal end of the cylindrical body. The number of the tip tools corresponds to the number of the cylindrical bodies. The tips tools are mounted onto the deployment wire and are axially displaceable thereby. The tip tool is configured to unwind at least one coiled thread, at times all of the coiled threads simultaneously, from its corresponding cylindrical body upon axial displacement of the tip tool, such that the wound coiled thread is unwound from its deployment state to at least one deployed state.

While each coiled thread has one deployment state, in which it is wound to form the cylindrical body, the thread may have several deployed states in which it gradually unwinds from the cylindrical body. The transition between the deployed states (i.e. the extent of deployment of the cylindrical body) occurs upon axial displacement of the tip tool and the relative positions of the tip tool and its associated cylindrical body along the deployment wire.

Unlike some of the thrombectomy devices known in the art, the anchoring unit of a system of this disclosure does not merely forms a net or a mesh of deployed wires that form physical barriers in the blood vessel and by that permits the retrieval of the corpus, but rather the corpus anchoring unit of the system of this disclosure anchors (i.e. penetrates into) the corpus at various locations thereof. Thus, and as also explained herein, the corpus anchoring unit of this disclosure does not need to be dimensioned to encompass the entire-cross section of the organ. This allows for both a relatively small unit (having a small volume imprint) when introducing the unit into the blood vessel, as well as a relatively small volume imprint of the deployed unit. Such small dimensions reduce the risk of possible damaging the blood vessel during the corpus's capturing and retrieval procedure.

Therefore, the presently disclosed systems also provide effective removal of occlusive corpus from a tubular organ while minimizing the risk of injury to the organ's wall during retrieval.

The HMA is configured to axially, at times also rotationally (as explained further below) displace the deployment wire, consequently axially and/or rotationally displacing at least one of the tip tools and/or the cylindrical bodies.

In the present disclosure, reference is made to proximal-distal directionality. In the system of the present disclosure, the deployment wire extends between a proximal end of the wire that is linked to the HMA, and a distal, typically free, leading-end of the wire. The proximal-distal axis is defined as the longitudinal axis extending between the wire's ends. Thus, the terms proximal and distal (or any lingual variation thereof), refer to the position of various elements along the proximal-distal axis. Accordingly, axial displacement is meant to refer to a movement of an element along the axis, whether in the proximal-distal direction or in the distal-proximal direction.

The wire is typically formed out of a biocompatible material, such as polymeric or metallic biocompatible materials known in the art. Examples of suitable materials include metal, metal alloy, a metal-polymer composite, combinations thereof, and the like, or any other suitable material.

Some examples of suitable metals and metal alloys include stainless steel, 316LV stainless steel; mild steel; nickel-titanium alloy such as linear-elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; combinations thereof; and the like; or any other suitable material.

In some embodiments, the wire is flexible. The wire has a diameter which is smaller than the diameter of the tubular organ, i.e. blood vessel, into which the corpus anchoring unit is inserted. By some embodiments, the diameter of the deployment wire is between about 0.0045 inches and 0.018 inches. It is of note that other dimensions are also contemplated.

The corpus anchoring unit may be inserted into the organ via a catheter, a micro-catheter or an endoscope. In some operational procedures, usually depending on the physical properties (i.e. geometry, density, etc.) of the corpus, a leading bore may be formed in the corpus by a preliminary stage using a designated tool. The leading bore enables subsequent insertion of corpus anchoring unit of the system of this disclosure, such that a part of the corpus anchoring unit penetrates beyond the corpus in the distal direction.

In cases where the corpus has suitable consistency, the system of this disclosure may be used to form such a leading bore. Namely, where the consistency of the corpus is suitable, the leading end of the wire may be used to penetrate through the corpus. In such embodiments, the leading end of the deployment wire may be tapered, slanted and/or grooved to permit penetration through the corpus. The leading end may be made of the same material as the wire or of a different material.

The HMA is configured to axially (and/or rotationally) displace the deployment wire, such that the corpus anchoring unit is brought into proximity with the corpus. Once in such proximity, the corpus anchoring unit is operated (i.e. deployed) by axial displacement the deployment wire induced by the HMA.

As noted above, the deployment wire is associated with at least two generally cylindrical elongated bodies (also interchangeably referred to herein as tubes), that may typically have the form of a hollow cylinder having a longitudinal axis, extending between a proximal tube end and a distal tube end. In some embodiments, the tubes are coaxial with said deployment wire.

As noted above, the cylindrical bodies comprise at least one, typically a plurality of, pre-stressed helically coiled threads, which are tightly wound and held one against the other to form a shape of the elongated cylindrical body (i.e. a tube). As the coiled threads are wound and interact with one another by friction forces, the cylindrical bodies do not need external arrangements to maintain the threads in the wound configuration. In other words, the cylindrical bodies are designed to have a normally-closed configuration in their deployment state, which require active engagement with the tip tool to transit into the deployed (unwound) state. This permits, as discussed and exemplified herein, highly controlled deployment of the threads during the corpus capturing process. Such a normally-closed configuration is contrary to common devices available on the market, in which the deployable units are configures to have a normally open configuration and are held in a collapsed state by external means (such as external sleeves or micro-catheters). Such units need to be inserted in the collapsed state, and upon removal of the external means they automatically and immediately deploy to their original normally-open configuration without interaction with an additional element—such automatic deployment is often uncontrolled and may cause damage to the blood vessel or fragmentation of the corpus. As already noted, such damage and/or fragmentation may be avoided by using the normally-closed tubes of the unit of this disclosure.

In some embodiments, the deployed threads are dimensioned to exert a radial force of no more than about 1 N (in a conduit having a diameter of 2 mm) on the internal surface of the organ.

In some embodiments, the number of cylindrical bodies (and hence the number of tip tools) is between 2 and 10. In other embodiments, the number of cylindrical bodies is 2, 3, 4, 5, 6, 7, 8, 9 or 10.

According to some embodiments, each cylindrical body, independently of the others, may have a length of between about 1 and 10 mm, more typically between 2 and 5 mm. In other embodiments, the cylindrical bodies have an internal diameter of between about 0.001 inches (0.0254 mm) and about 0.13 inches (3.302 mm).

Each cylindrical body may independently be constituted of a different number of threads. Thus, in some embodiments, each cylindrical body, independently of the others, may comprise between 1 and 120 wound coiled threads. In other embodiments, the number of threads in each cylindrical body is independently between 1 and 80, or between 1 and 40, or between 1 and 20, or between 1 and 10, or even between 1 and 8 threads. In other embodiments, each cylindrical body in the anchoring unit consists of the same number of threads.

Each of the cylindrical bodies, independently of the others, may be a single layer tube or a multiple-layered tube. Namely, the wound coiled threads may be arranged in a single layer to form a single layer tube. Alternatively, several layers (typically between 2 and 5 layers) of wound coiled threads may be stacked to form a multi-layered tube. In the multi-layered tube, the layers may be arranged such that the threads of one layer are parallel to the threads of the subsequent layer. In another arrangement, the layers are arranged such that the wound coiled threads in at least one layer are off-set to the threads of a subsequent layer. Another arrangement permits variability in wounding direction, the threads in all of the layers may be wound in the same direction; or in at least one layer the threads are wound clockwise, while at an adjacent layer the threads are wound counter-clockwise. Such multi-layering enables tailored flexibility of the tubes as well as permits multi-stage deployment of the threads.

In some embodiments, the threads are made of a shape-memory metal or alloy, for example nitinol or stainless steel, such that their transition from the wound to the unwound state (i.e. from the deployment to the deployed state) is facilitated by the shape-memory properties of the alloy. In other embodiments, the threads have a wound deployment state and an unwound deployed state, and may be biased to the unwound deployed state. However, as noted above, the transition from the wound state to the unwound state is not spontaneous, and requires a mechanical engagement to overcome the friction forces between the wound threads. The threads are held together in the wound state by compression and friction resulting from the geometry of the cylindrical body and friction forces between the threads, and assume the unwound state upon axial displacement of the tip tools, as explained herein.

The term free end, or open end, which is at times also interchangeably referred to herein as opening end, refers to an end of the cylindrical body in which unwinding of the coiled threads is enabled. Meaning, that once unwinding occurs, unwinding will advance from the free end to the opposite end of the tube. As can be appreciated, the free end is not fixedly attached to the deployment wire. According to some embodiments, an opposite end of the tube, being the fixed end, is configured to maintain a section of the threads in a wound, coiled state, thereby preventing their deployment at the fixed end. In such embodiments, once unwound, the section near the opening end of the tube will be in an unwound state, while the section of the threads near the opposite (fixed) end will be maintained in a wound state. Maintaining the fixed end in the wound state may be enabled by any suitable means known in the art, for example, by fixedly associating the fixed end to the deployment wire, locally welding the threads one to the other, by association with an external or internal unwinding limiting element, etc.

According to some embodiments, at least one of the cylindrical bodies has a free, open end. In other embodiments, in each cylindrical bodies one of the proximal or distal ends is a free, open end. In such embodiments, the distal ends may be said open ends. In other such embodiments, the proximal ends may be said open ends. In some other embodiments, in all cylindrical bodies (i.e. all of the tubes) the proximal end is the open end; according to other embodiments, in all tubes the distal end is the open end.

According to some embodiments, the cylindrical bodies may be arranged along the deployment wire (from the proximal to the distal end) such that (i) odd cylindrical bodies have free ends at respective distal ends, while even cylindrical bodies have free ends at respective proximal ends, or (ii) odd cylindrical bodies have free ends at respective proximal ends, while even cylindrical bodies have free ends at respective distal ends.

According to some embodiments, external surface of at least one of the cylindrical bodies may enveloped by a restricting layer, which may be constituted by a polymeric layer or sheet, that is positioned along a portion of the tube's length (however not over the entire length of the tube). The enveloped portion of the cylindrical body is typically distanced along said deployment wire from the free end of the cylindrical body. Typically, such restricting layer will be positioned to envelope a mid-portion of the cylindrical body, that encompasses no more than a half, at times a third, of the body's length. This restricting layer limits (or restricts) the extent of unwinding of the coiled threads. Such a restricting layer may be made of a flexible material that will permit deformation of the cylindrical body when the tip tool engages the restricted portion of the cylindrical body. Non-limiting examples of such materials may be polymeric materials, which may be selected from polytetrafluoroethylene (PTFE), polyethylene, polypropylene, polyurethanes, and others.

Such a restricting layer may be designed to enable deployment of the threads in two stages, by varying the force required to unwind the threads in different sections of the cylindrical body. Namely, a first stage of deployment will require an initial force in the non-restricted section of the cylindrical body to permit unwinding of the threads to a first length, and second stage of deployment that requires a larger applied force for further deployment in the restricted section of the cylindrical body, thus unwinding the threads to their final desired deployed length. Such two-stage deployment may be used for controlling and timing of the desired deployment sequence. It is to be understood that the restriction layer may not be present in all of the cylindrical bodies. Further, the restricting layer, if such exists, may vary from tube to tube (e.g. in the type of material, thickness, length, etc.) to allow tailoring of the deployment sequence.

As explained herein, the unwinding of the threads results in anchoring of the unwound coiled thread in the corpus by a helical movement (i.e. an axial-rotational or screw-like movement) of the thread during its unwinding. In other words, due to its helical geometry, during the transition of the thread from its wound deployment state to its unwound deployed state, a leading free end of each thread displaces in an axial-rotational manner (i.e. screw-like movement), to trace a generally helical path and is anchored into the corpus.

In the corpus anchoring unit, each cylindrical body is associated with a corresponding tip tool, such that the tip tool is typically positioned at the free end (being either the proximal or the distal end) of its corresponding cylindrical body. In some embodiments, the tip tool is in abutment or in contact with the free end of its corresponding cylindrical body. The axial displacement of the tip tool (induced by the HMA), causes the threads in the cylindrical body associated with the tip tool to unwind.

The tip tool typically has an ellipsoid or tear-drop shape, such that the longitudinal axis of the tip tool coincides with the deployment wire. The tip tool may have a maximal diameter similar to that of the cylindrical body. In some embodiments, the maximal diameter of the tip tool is larger than the internal diameter of the associated cylindrical body, such that the maximal diameter of the tip tool will allow only partial penetration of the tip tool into the cylindrical body's lumen.

In some embodiments, the tip tool further comprises a tubular element associated with one of its proximal or distal ends. As will also be discussed and demonstrated below, the tubular element functions to further control the unwinding of the wound coiled threads. When the tip tool is displaced into the cylindrical body, the angle of impact of the free edges of the wound threads with the tubular element, which may be varied by varying the dimensions of the tear-shaped section of the tip tool, results in a variance in the mechanical force applied on the free edges of the wound threads. Therefore, by varying the dimensions of the tip tool, one mechanism to control the force required for deployment of the tubes may be obtained.

Another parameter that may have an influence on the applied force to cause unwinding is the dimensions of the ellipsoid section of the tip tool. For example, and without wishing to be bound by theory, the tip tool may be in the form of an tri-axial or oblate ellipsoid, wherein the relation between its semi-principle axes dimensions determines the angle at which the surface of the tip tool engages its corresponding cylindrical body. Various angles may transfer different loads (and hence difference forces) to the cylindrical body. Other deployment control mechanisms are detailed below.

According to some embodiments, the tip tools are positioned at the distal end. In other embodiments, the tip tools are positioned at the proximal ends. According to some other embodiments, at least one of the tip tools is positioned at a proximal end of its corresponding cylindrical body and at least one other tip tool is position at a distal end of its corresponding cylindrical body.

According to some embodiments, when the proximal end of the cylindrical body is the open, free end, the tip tool may be displaced in the distal direction to unwind at least one thread from the cylindrical body. According to other embodiments, when the open, free end is a distal end of the cylindrical body, the tip tools may be displaced in the proximal direction to unwind at least one thread from the cylindrical body.

In some embodiments, the tip tool is made of a biocompatible material know to a person of skill in the art. Some non-limiting examples are tip tools made of metal, metal alloys, soldering compositions, polymers, or polymer-coated metals. In other embodiments, the tip tool may be made from a different material from that of the cylindrical body's threads. In order to assist in monitoring the corpus anchoring and extraction process, at least one of the tip tools may comprise an radiopaque marker, e.g. a platinum iridium (Pt—Ir) or gold marker.

As noted above, the tip tools are associated with the deployment wire, such that operation of the HMA induces axial displacement of the tip tools, thereby eventually leading to selective unwinding of the threads from the tubes, as explained herein.

In order to permit such selective unwinding, in some embodiments, each cylindrical body is independently configured to unwind at a force applied thereto upon axial displacement of the tip tool. In some embodiments, each of the cylindrical bodies unwinds at a different force applied thereto. The force applied by the axial displacement of the tip tool may be selected, controlled and/or adjusted by the HMA via the deployment wire.

In some embodiments, the force required for unwinding the threads is determined by the winding pitch of the coiled threads in the cylindrical body. By way of example, a coiled thread having a pitch of less than 45 degrees will require less force to initiate unwinding, while a coiled thread having a pitch higher than 45 degrees will require a larger applied force for unwinding.

Another way to control the force required to unwind the threads is varying the thickness of the threads. Namely, the thicker the threads are, the more resistant they are to unwinding, and hence a larger force will be required for unwinding. Similarly, the tubes may be made of materials having different moduli of elasticity, such that for low modulus materials unwinding will require application of less force than for threads made of a higher modulus material.

An additional means for controlling the sequence of opening is by eliminating some of the threads composing the cylindrical body, e.g. by using a grooved tube wherein one or more of the threads have been removed. Without wishing to be bound by theory, a reduced number of threads results in less friction between the threads, requiring application of smaller forces to overcome the friction between the threads and cause their unwinding.

Any number of threads can be removed from the cylindrical body to obtain a grooved tube, for example, one thread, or two threads, or three threads, or four threads, or five threads, or six threads, or seven threads and so on. The number of threads that can be removed is between 1 and the total number of threads in the cylindrical body minus 1 (i.e. n−1). In some embodiments, the number of threads removed is two.

As any person of skill in the art would appreciate, the mechanism that enables variance in required unwinding force may be one of the above or any combination thereof.

As noted above, the unwinding of the threads is caused by axial displacement of the tip tools associated with the deployment wire. In some embodiments, at least one of the cylindrical bodies is fixedly associated with said deployment wire. In other embodiments, at least one of the cylindrical bodies is floating. According to some other embodiments, at least one of the tip tools is fixedly associated with said deployment wire. According to further embodiments, at least one other of the tip tools is floating.

The term floating is meant to denote that the element is not in direct contact with the deployment wire, such that relatively low friction axial displacement (i.e. sliding) is enabled. Such floating may be obtained, for example, by coating at least a portion of the deployment wire by layer having a low friction coefficient, such that the layer becomes interposed between the wire and the elements mounted thereon (i.e. the tubes and the tip tools). However, as may be appreciated, other possible means known to a person of skill may be applicable.

In some embodiments, the distal cylindrical bodies are fixedly associated with said deployment wire and proximal cylindrical bodies are floating. In other embodiments, the proximal cylindrical bodies are fixedly associated with said deployment wire and distal cylindrical bodies are floating. In such embodiments, floating tip tools may be associated with fixedly-associated cylindrical bodies, and floating cylindrical bodies may be associated with fixedly-associated tip tools.

According to some embodiments, the cylindrical bodies are spaced apart by a spacer, which may, for example, be constituted by a rigid tube of defined length or by sections of the deployment wire having larger diameter than the rest of the wire. In some embodiments, the spacing between cylindrical bodies is at least 2 mm.

In order to facilitate increased capturing of the corpus, by some embodiments, the threads comprising at least one of the cylindrical bodies are coiled in a direction permitting their unwinding helical movement in one rotational direction (e.g. clockwise or counterclockwise) upon axial displacement of the corresponding tip tool.

According to additional embodiments, (i) the threads comprising at least one of the cylindrical bodies may be coiled to permit helical unwinding in one rotational direction upon axial displacement of its corresponding tip tool, and (ii) the threads comprising a consecutive cylindrical body along the proximal-distal axis may be coiled to permit their helical unwinding in an opposite rotational direction upon axial displacement of its corresponding tip tool. In cases where the corpus anchoring unit is made of pairs of cylindrical bodies, such arrangement permits a "cage" formation that captures the corpus from both the distal and the proximal direction. Further, in such arrangements, the threads in each tube may vary in length in order to allow their tangling during or after unwinding. Namely, the distal cylindrical body in a pair of cylindrical bodies may consist of shorter threads, while the proximal cylindrical body may consist of longer threads (and vice versa).

In another variant of the corpus anchoring unit in a system of this disclosure, the cylindrical bodies are arranged in oppositely-oriented pairs, such that a plurality of cage structures are formed upon deployment of the cylindrical bodies.

Thus, in another aspect, there is provided a medical system for anchoring into at least one corpus located in a tubular organ, the system comprising a handling and manipulation apparatus (HMA) and a corpus anchoring unit operable thereby, the HMA being configured for manipulating the corpus anchoring unit into engagement with said corpus, the corpus anchoring unit comprising:
  a deployment wire defining a proximal-distal axis;
  at least one pair of generally cylindrical elongated bodies spaced apart along said deployment wire, each of said bodies having a proximal end and a distal end, and being constituted by at least one wound coiled thread in a deployment state, a first of the pair of bodies being a proximal body with a proximal fixed end and a distal free end and a second of the pair of bodies being a distal body with a distal fixed end and a proximal free end, the free end of each body being configured for deploying into a deployed state in which each of the threads unwinds in the general radial direction while tracing, during deployment, a generally helical path, and
  at least one pair of axially displaceable tip tools, each mounted onto the deployment wire at the body's free end, such that axial displacement of the tip tool forces the wound coiled threads to unwind into said at least one deployed state,
the HMA being configured to axially (and/or rotationally) displace the deployment wire.

In some embodiments, the unwinding of the coiled threads of each pair of cylindrical bodies causes entanglement of the unwound threads of one of the bodies into the unwound threads of the other body of said pair. Namely, the unwound threads of each pair of cylindrical bodies form a cage structure.

Such systems may comprise at least 2 pairs of cylindrical bodies, namely 4, 6, 8 or even 10 cylindrical bodies (and hence 4, 6, 8, or even 10 tip tools associated therewith). In some embodiments, the length of the first cylindrical body of each pair of cylindrical bodies is larger than the length of the second cylindrical body of each pair of cylindrical bodies. Namely, the proximal tube in each pair is configures to have longer unwound coiled threads than its corresponding distal tube. As typically the direction of retrieval is movement in the distal-to-proximal direction (once the corpus has been captured), i.e. pulling of the deployment wire, such an arrangement will limit, and at times prevent, contact of the free edges of the distal deployed coiled threads with the inner face of the blood vessel, thereby minimizing and even preventing further damage to the blood vessel.

In addition to the pairs of cylindrical bodies, such systems can further comprise at least one additional (stand-alone) cylindrical body, spaced apart from said at least one pair of cylindrical bodies on the deployment wire, the additional cylindrical body being associated with an additional tip tool at a proximal end or a distal end of the additional cylindrical body. The additional cylindrical body may be used to further anchor an end of the corpus or function to capture emboli.

Typically, in systems comprising pairs of cylindrical bodies, (i) the threads of one cylindrical body of the pair may be coiled to permit their helical unwinding in one rotational direction upon axial displacement of its corresponding tip tool and (ii) the threads of the other cylindrical body of said pair may be coiled to permit their helical unwinding in an opposite rotational direction upon axial displacement of its corresponding tip tool. Thus, in addition to deployment in different proximal-distal orientations, the unwinding of the coiled threads in a pair of such cylindrical bodies also results in oppositely rotational helical movements of the free ends of the threads during their unwinding (e.g. a clockwise rotation in one cylindrical body and an anti-clockwise rotation in the other cylindrical body), thereby enhancing penetration of the unwound coiled threads into the corpus and applying torque forces onto the corpus, that result both in stronger anchoring and compactization of the corpus.

It is of note that in embodiments where a plurality of pairs of tubes are utilized, each pair may form a cage structure (i.e. a primary cage). Once two such primary cages are brought into proximity one with the other, a secondary, larger cage may be formed. Therefore, with each proximating cage, the distance between such cages is shortened, further compacting the corpus and assisting in its retrieval.

It is further of note that the formation of cages permits a stable anchoring into the corpus; thus, if by any reason tension on the deployment wire is released (or slack is formed in the wire), the cages will remain anchored within the corpus due to the interlocking interaction of the unwound threads of two adjacent deployed cylindrical bodies.

In some embodiments, the corpus anchoring units of the systems described herein may further comprise at least one closed tube. The closed tube(s) mean to denote tubes made of a plurality of wound coiled threads, configured such that in both the proximal end and the distal end of the tube the threads are fixedly coupled one to the other. Each such closed tube may be associated with a tip tool, associated with either a proximal or distal end of the closed tube. Upon pulling (or pushing) the deployment wire, the tip tool will apply force onto the distal (or proximal) end of the tube, causing the distal end and the proximal end to proximate one another; since the threads are held together at the ends of the tube, such applied force will cause the tube to radially expand as a result of the shortening in length. Such deployed closed tubes may form a barrier to reduce the risk of embolization or allow local controllable expansion of the blood vessel's diameter.

The closed tube may be grooved, i.e. one or more of the threads may be removed in order to obtain a grooved tube. In such configurations, several distinct radially expanded sections of the closed tube may be obtained once the tube is deployed. The number of threads removed and/or their position will determine the distance between expanded sections, and at times also the maximal radial expansion possible for each section of the tube.

To provide further reduction in the risk of embolization of the thrombotic material during endovascular recanalization procedures may be obtained by inclusion of one or more embolic protection elements. Thus, in some embodiments, the system may further comprise at least one embolic protection element, which may be positioned proximal and/or distal ends of the corpus anchoring unit.

One non-limiting example of such embolic protection elements include an occlusion balloon, displaceable over a wire proximal to the thrombus in order to trap and aspirate thrombotic debris released during the thrombectomy procedure. Another non-limiting example may be an occlusion balloon or a filter displaceable over a wire distal to the thrombus, permitting trapping and aspiration (or capture and retrieve) thrombotic debris released during the thrombectomy procedure.

In another embodiment, the embolic protection element may be a protective sleeve that forms a closed or partially-closed cover surrounding the thrombus during retrieval. In another embodiment, the cover may further provide protection and support to the vessel wall, reducing the risk of vessel wall injury during retrieval. The cover may have a fixed section at the proximal end of the corpus anchoring unit, and a free section extending in a proximal direction. The cover may have a diameter equal or greater that the corpus anchoring unit. There may be friction between the cover and the vessel wall resisting proximal movement of the cover, causing the cover to avert over the corpus anchoring unit, permitting the free section of the cover to be distal to the capturing zone. Averting refers to inside-out turning of the cover due to movement of the corpus anchoring unit within the cover, causing the cover sleeve to protects and cover the corpus anchoring unit.

In some embodiments, the embolic protection element may be expandable through self-expanding configurations, or via actuated expansion (e.g., a shape memory alloy, spring expansion, or other actuation), or any other suitable mechanism known in the art. Similar to the elements of the corpus anchoring unit, the embolic protection element(s) may include radiopaque markers, such as gold and platinum for improved visibility under fluoroscopic imaging. The embolic protection element may be made of any suitable material known in the art, for example, biocompatible polymer sheet, biocompatible metal or alloy, etc.

It is of note that at least one, optionally at least some, or even all of the elements of the corpus anchoring unit (i.e. the deployment wire, the cylindrical bodies, the tip tools, the embolic protection element, and/or any other element being part of the corpus anchoring unit), as well as elements of the HMA which are inserted and/or come into contact with bodily tissues, may be coated by a suitable biocompatible coating. For example, a polymeric coating, a hydrophilic coating etc.

Although some specific examples are provided above with respect to the materials from which the different system's parts may be made of, it is noted that such examples are non-limiting. Namely, the different part of the system may independently comprise metals, polymers, ceramic materials; may comprise non-bioabsorbable and/or bioabsorbable materials; some or all of the elements coming into contact with bodily tissues may elute desired substances over time (such as drugs, biologics, anti-thrombotics, coagulants, anti-coagulants, anti-inflammatory drugs, thrombolytic drugs, anti-proliferative drugs, healing promotors, re-endothelialization promoters, or others).

The handling and manipulation apparatus (HMA) may comprise an actuator associated with a shaft pipe. As used herein the term shaft pipe denotes an elongated, typically tubular, element, which may be made of any material that can withstand or resist compression loads along the longitudinal axis, for example stainless steel. The shaft pipe typically has a longitudinal lumen, through which the deployment wire is threaded. The shaft pipe may be fixedly coupled at its proximal end to the actuator via a shaft pipe handle, and at its distal end to one or more of the cylindrical bodies. The shaft handle on the actuator allows pushing or rotation of the shaft tube, thereby affecting the unwinding of the threads or allowing the helical (i.e. axial-rotational) movement of unwound threads of threads, controlling the coil pitch of the winding and allowing increase of the outside diameter of the cylindrical bodies.

The HMA is configured to associate with the deployment wire of the corpus anchoring unit, such that the corpus anchoring unit is operable by the HMA. The term operable denotes the manipulation of the corpus anchoring unit into engagement with the corpus in the conduit, axial movement of the tip tools, unwinding of the cylindrical bodies at a desired sequence for anchoring into the corpus, and extracting the corpus.

Thus, the actuator may be used to operate the corpus anchoring unit for anchoring and retrieval of a corpus disposed in the tubular organ. In an exemplary embodiment, the actuator may comprise two types of handles: a deployment wire handle that is fixedly coupled to the proximal end of the deployment wire, and a shaft pipe handle that is fixedly coupled to the shaft pipe of the HMA. The actuator is designed to allow the following exemplary types of movements:

1. Rotation of the deployment wire—to allow rotation of unwound threads, to control the coil pitch of the threads, and to allow increase of the outside diameter of the cylindrical bodies. Further, rotation of the deployment wire allows for centralizing the corpus anchoring unit during insertion of the device (i.e. guide the corpus anchoring unit from a position between the blood-vessel inner wall and the clot into a centralized position within the blood clot), thereby increasing the efficiency of anchoring during deployment of the cylindrical bodies.
2. Axially pulling/pushing the deployment wire—to allow axial displacement of the tip tools and subsequently unwinding of threads
3. Rotation of the shaft or the deployment wire—to control navigation of the wire's leading end and the corpus anchoring unit, and to facilitate the unwinding of the threads.

Applying variable torque onto the different elements mounted onto the wire is also contemplated and within the scope of the present disclosure.

The system of this disclosure may be provided as a unitary system. Namely, in another aspect, this disclosure provides a kit comprising a system as described herein an instructions for use.

Alternatively, the HMA and the corpus anchoring unit may be provided separately, and the practitioner associates between the HMA and the corpus anchoring unit prior to utilization. Such separate corpus anchoring unit enables replacement of the corpus anchoring unit at will. Thus, in an aspect, the disclosure provides a kit comprising a handling and manipulation apparatus (HMA), at least one corpus anchoring unit, and instructions for assembly and/or use.

Further, the corpus anchoring unit may also be provided as separate element for self-assembly, enabling variance in the amount of operable elements and/or their sequence along the deployment wire. Thus, in another aspect, this disclosure provides a kit for assembly of the system as herein described, comprising a handling and manipulation apparatus (HMA); at least one deployment wire; a plurality of cylindrical bodies, each cylindrical body being constituted by at least one shape-memory metal or alloy wound coiled thread; a plurality of tip tools; instructions for assembly; and optionally comprising a plurality of spacers.

In some embodiments, the kit further comprises means for associating the deployment wire with (i) the HMA, (ii) the cylindrical bodies, and/or (iii) the tip tools.

Another aspect of this disclosure provides a method for removal of a corpus located in a tubular organ, comprising:
(a) manipulating a corpus anchoring unit by a handling and manipulation apparatus (HMA) associated therewith, such that the corpus anchoring unit is brought into proximity with the corpus, the corpus anchoring unit comprising:
    a deployment wire defining a proximal-distal axis;
    at least two generally cylindrical elongated bodies that are spaced apart along said deployment wire, each body having a proximal end and a distal end and being constituted by at least one wound coiled thread in a deployment state, each of said bodies having a fixed end at either the proximal or distal end and having a free, opposite end that is configured for deploying into at least one deployed state in which each of the threads unwinds in the general radial direction while tracing, during deployment, a generally helical path and
    at least two axially displaceable tip tools, each mounted onto the deployment wire and associated with the free end of the bodies;
(b) axially displacing the deployment wire to axially displace at least one tip tool, thereby unwinding at least one coiled thread from its associated body from the deployment state to said at least one deployed state, thereby anchoring the unwound coiled thread into the corpus; and
removing the anchored corpus from the organ by manipulating the corpus anchoring unit out of the organ.

Another aspect of this disclosure provides a method for removal of a corpus located in a tubular organ, comprising:
(a) manipulating a corpus anchoring unit by a handling and manipulation apparatus (HMA) associated therewith, such that the corpus anchoring unit is brought into proximity with the corpus, the corpus anchoring unit comprising:
    a deployment wire defining a proximal-distal axis;
    at least one pair of generally cylindrical elongated bodies that are spaced apart along said deployment wire, each body having a proximal end and a distal end and being constituted by at least one wound coiled thread in a deployment state, a first of the pair of bodies being a proximal body with a proximal fixed end and a distal free end and a second of the pair of bodies being a distal body with a distal fixed end and a proximal free end, the free end of each body being configured for deploying into a deployed state in which each of the threads unwinds in the general radial direction while tracing, during deployment, a generally helical path, and at least one pair of axially displaceable tip tools each mounted onto the deployment wire, a first of said pair of tip tools being associated with the distal free end of the first of the pair of bodies, and a second of said pair of tip tools being associated with the proximal free end of the second of the pair of bodies, (b) axially displacing the deployment wire in the proximal direction to axially displace the first tip tool in the proximal direction, thereby unwinding at least one coiled thread from the first body from its deployment state to at least one deployed state, thereby anchoring the unwound coiled thread into the corpus;

(c) axially displacing the deployment wire in the proximal direction to axially displace the second tip tool in the proximal direction, thereby unwinding at least one coiled thread from the second body from its deployment state to at least one deployed state, thereby anchoring the unwound coiled thread into the corpus; and removing the anchored corpus from the organ by manipulating the corpus anchoring unit out of the organ.

In some embodiments, the system comprises two or more pairs of cylindrical bodies and steps (b)-(c) are repeated for each such pair. Namely, steps (b) and (c) are carried out for the first pair, then steps (b) and (c) are carried out for another pair, and so forth.

In other embodiments, the methods may further comprise a step (c'), carried out between steps (c) and (d), that comprises (c') axially displacing the deployment wire to bring the second cylindrical body into proximity with the first cylindrical body, thereby forming a cage structure, and optionally entangling the unwound coiled threads of the second cylindrical body and the unwound coiled threads of the first cylindrical body.

In such embodiments, the method may further comprises a step (c"), carried out between step (c') and (d), that comprises (c") axially displacing the deployment wire to bring two adjacent cage structures into proximity with one another.

Another aspect provides a system as described herein for use in removing a corpus from an anatomical conduit.

As used herein, the term "about" is meant to encompass deviation of ±10% from the specifically mentioned value of a parameter, such as length, diameter, force, etc.

Whenever a numerical range is indicated herein, it is meant to include any cited numeral (fractional or integral) within the indicated range. The term "between" or "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be noted that the range is given as such merely for convenience and brevity and should not be construed as an inflexible limitation on the scope of the invention. Accordingly, the description of a range should be considered to have specifically disclosed all the possible sub-ranges as well as individual numerical values within that range.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 13A shows the occlusive thrombus extending into branches of the IMA artery;

FIG. 13B shows the 8F guiding catheter 0.014" wire crossing the occlusive thrombus;

FIG. 13C shows a 0.017" micro-catheter navigated over the 0.014" wire crossing the occlusive thrombus;

FIG. 13D shows the device crossing the occlusive thrombus, with three distal radiopaque markers positioned distal to the thrombus;

FIG. 13E shows the occlusive thrombus trapped and retrieved using the device, pulled back into the guiding catheter. During deployment of the device, the deployed tubes proximate one another and compressed against each other, resulting in compression of the occlusive thrombus; and FIG. 13F shows achievement of full recanalization of the artery (zoom: 123%).

FIG. 14A shows the occlusive thrombus extending into branches of the IMA artery;

FIG. 14B shows the device crossing the occlusive thrombus, with three distal radiopaque markers positioned distal to the thrombus and deployed;

FIG. 14C shows the first portion of the occlusive thrombus is trapped and retrieved using the device and is pulled back into the guiding catheter;

FIG. 14D shows entrapment of the second portion of the occlusive thrombus; and

FIG. 14E shows achievement of full recanalization of the artery.

DETAILED DESCRIPTION OF EMBODIMENTS

As described above, the system of this disclosure includes a handling and manipulation apparatus (HMA) and a corpus anchoring unit operable thereby. The corpus anchoring unit is typically inserted into the vessel to be treated in a non-deployed state via a pre-inserted catheter or microcatheter. Once reaching the corpus to be extracted, the corpus anchoring unit is deployed for anchoring into the corpus, to enable its extraction from the vessel.

Figure 1:
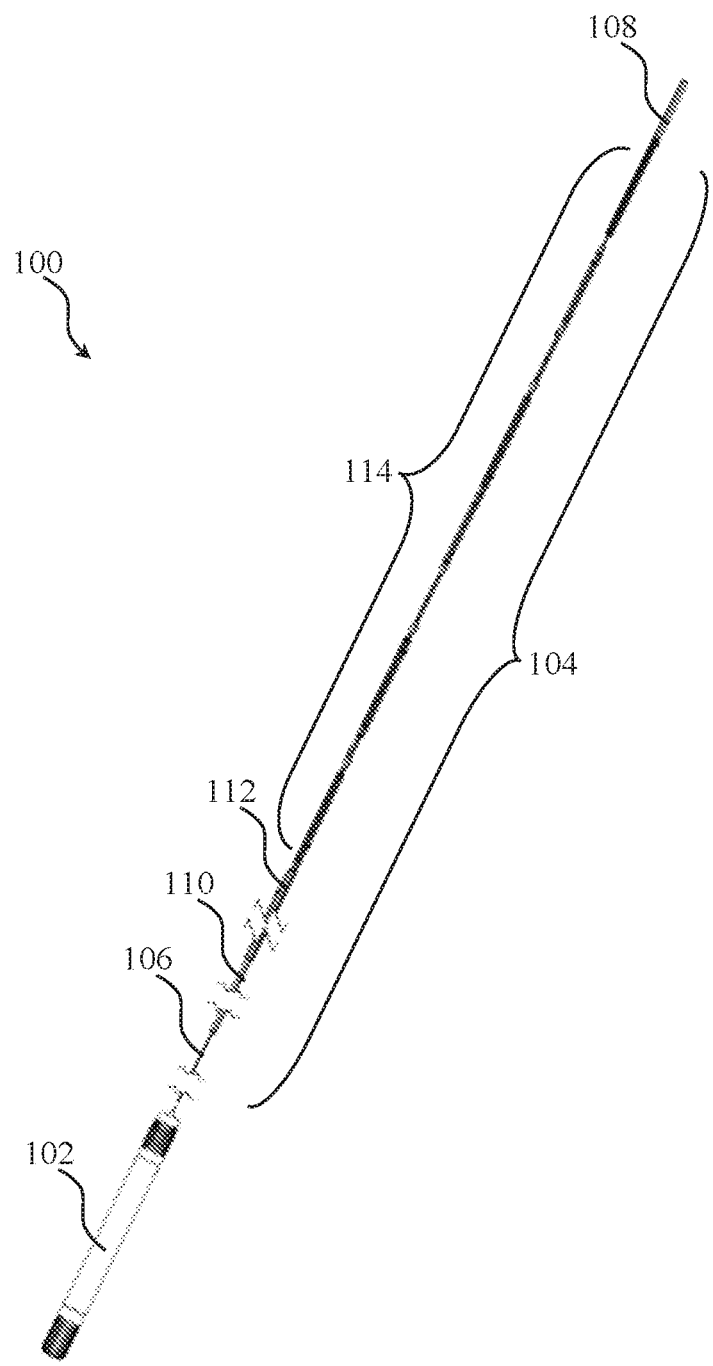
FIG. 1 shows a perspective view of the device according to this disclosure.

Turning first to FIG. 1, a system 100 according to an embodiment of this disclosure is depicted. The system includes an exemplary HMA unit 102 and a corpus anchoring unit, generally designated 104. It is of note that the HMA may have various designs (not shown), and the functionality of the HMA is not limited by any specific external design.

The corpus anchoring unit comprises a deployment wire 106, extending from the HMA unit 102 to the flexible distal end 108 of the corpus anchoring unit. The wire is typically made of a flexible biocompatible material, which may, for example, be a metal, an alloy or a polymer material. Onto the wire, various functional unit parts are mounted, in a manner allowing insertion and navigation of the corpus anchoring unit within the vessel, as well as the unit's deployment for anchoring, entrapping and extracting of the clots, as will be described below.

The HMA further includes a main tubular pipe shaft 110 and a flexible tubular pipe shaft 112, both mounted onto the deployment wire, typically coaxially therewith. Namely, the wire 106 is threaded through a longitudinal lumen formed within main pipe 110 and flexible pipe 112, such that the wire may be pulled and pushed through the pipes. The main pipe is typically made of a material having limited flexibility, for example a biocompatible alloy such as nitinol, and is use to impart mechanical strength to the corpus anchoring unit upon insertion and extraction.

Associated to the distal end of pipe 110 is flexible pipe 112; pipe 112 has increased flexibility (compared to pipe 110), and allows improved positioning of the deployable section 114 of the corpus anchoring unit. Both pipes 110 and 112 have a diameter which is sufficient for free movement of the wire 106 and the associated deployable section 114, both in the non-deployed state and in the deployed state for extraction of the entrapped clot.

Figure 2:
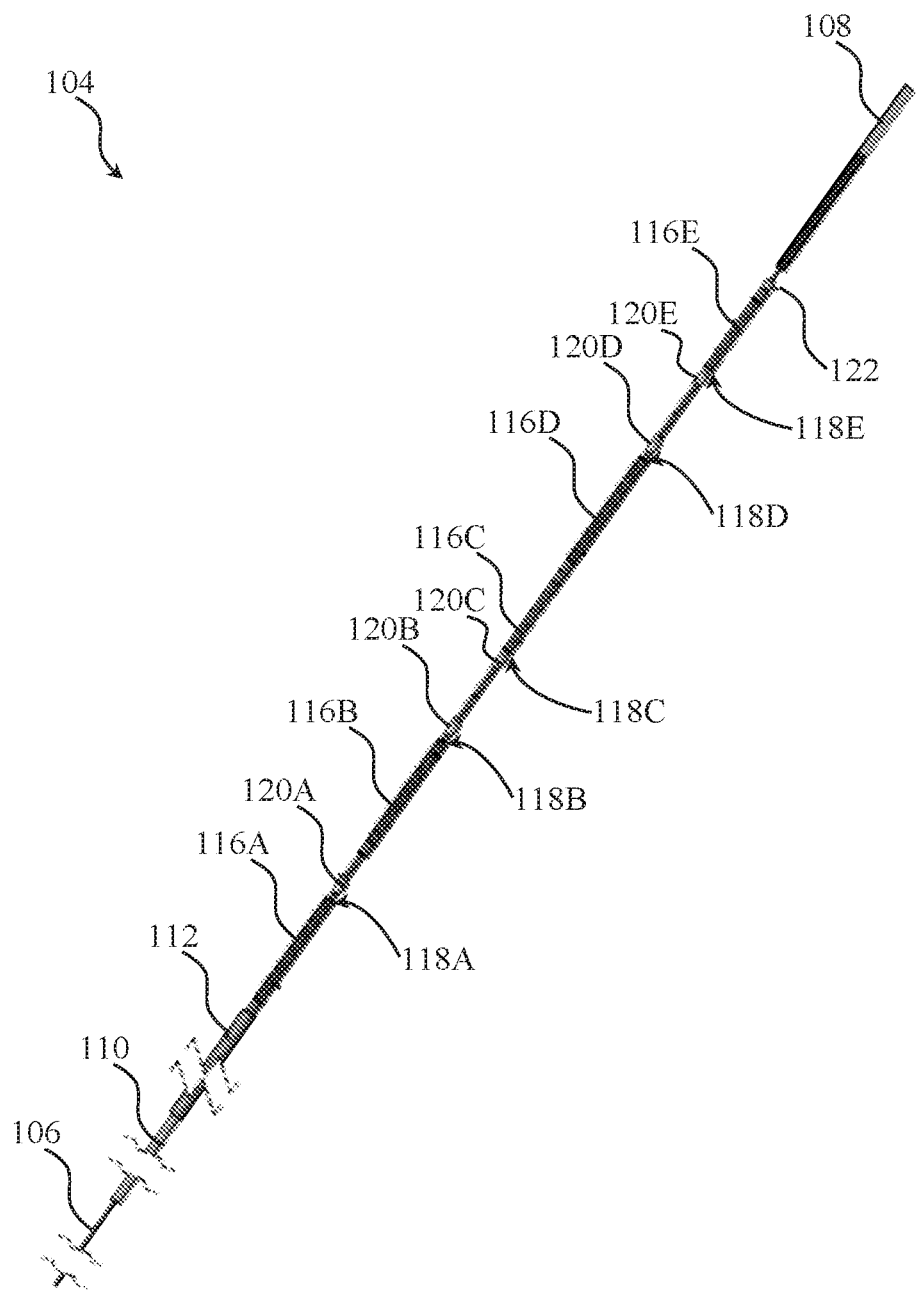
FIG. 2 is a close-up view of the device of FIG. 1 in the deployment (i.e. non-deployed) state of the cylindrical bodies (i.e. the tubes).

The deployable section 114 of the corpus anchoring unit is positioned distally to the flexible pipe 112. A close-up view of the corpus anchoring unit can be seen in FIG. 2. The deployable section 114 comprises at least 2, in this specific example 5, deployable cylindrical bodies 116A-116E (i.e. 5 tubes), each of the cylindrical bodies having an open, free end 118A-118E, respectively, positioned either at the proximal or distal end of each cylindrical body. Each of the cylindrical bodies is constructed out of a plurality of wound coiled threads, held together in the deployment state of the cylindrical body by friction forces. The cylindrical bodies are coaxially mounted onto the wire 106. Associated with each open free end 118A-118E are respective tip tools 120A-120E, which enable deployment of the threads, as will be explained further below.

Positioned distally to the outmost distal cylindrical body is a stopper 122. The stopper is fixedly attached to wire 106. Once the corpus anchoring unit is brought into proximity with the blood clot in the vessel, the system is operated to switch the corpus anchoring unit from the deployment to its deployed state. Several such states are shown in FIGS. 3A-3C.

The manner by which the corpus anchoring unit is deployed will now be described. Upon positioning of the corpus anchoring unit in adequate proximity to a corpus within vessel lumen, the wire 106 is manipulated by the HMA 102, such that movement of the wire switches the cylindrical bodies from a deployment state to a deployed state. Such manipulation typically involves pushing and/or pulling the wire 106 (torqueing the wire is also contemplated). Pulling on the wire causes fixedly attached stopper 122 to bear onto the outmost distal cylindrical body (in the exemplified embodiment cylindrical body 116E). As at least some of the elements mounted onto wire 106 are floating (i.e. not fixedly attached to the wire), the pulling force applied by stopper 122 onto cylindrical body 116E causes all mounted elements of the corpus anchoring unit to proximate one another, and transfer the pulling force between the mounted elements.

Figure 3A:
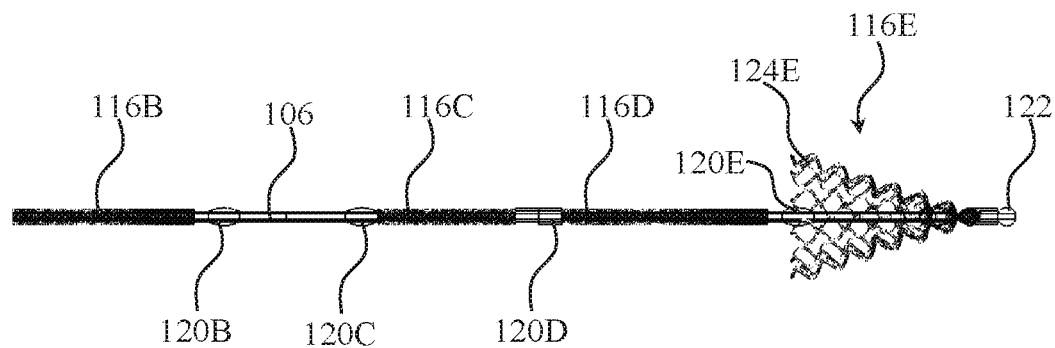
FIGS. 3A-3C show various deployment configurations of the unwound coiled threads (i.e. in a deployed state of the tube(s)): deployment of a single, distal tube (FIG. 3A); deployment of several tubes in the same opening orientation (FIG. 3B); and deployment of several tubes having different opening orientations (FIG. 3C).

In the example embodied by FIG. 3A, when the wire 106 is pulled, stopper 122 bears onto the fixed (closed) end of cylindrical body 116E, thereby causing cylindrical body 116E to move in the proximal direction. Such movement causes the open, free end of cylindrical body 116E to engage, or come into contact with, tip tool 120E, which in turn exerts an opposite force onto the open end of cylindrical body 116E. As the coiled threads of the cylindrical body are biased into their unwound state, the force exerted by tip tool 120E onto the open end is sufficient to switch the threads from their wound to their unwound state, resulting in deployment of cylindrical body 116E. As can be seen in FIG. 3A, the threads are welded to one another at the opposite end of cylindrical body 116E (i.e. the fixed end opposite the open, free end), preventing the threads from completely unwinding. This results in a cone-like or funnel-like arrangement of the unwound threads that permits physical capturing of the clot once the cylindrical body is deployed and preventing the clot from drifting further into the blood vessel. Further, to the physical encaging of the clot, the unwinding movement of the threads during unwinding will cause the threads to penetrate the clot and anchor it.

Figure 3B:
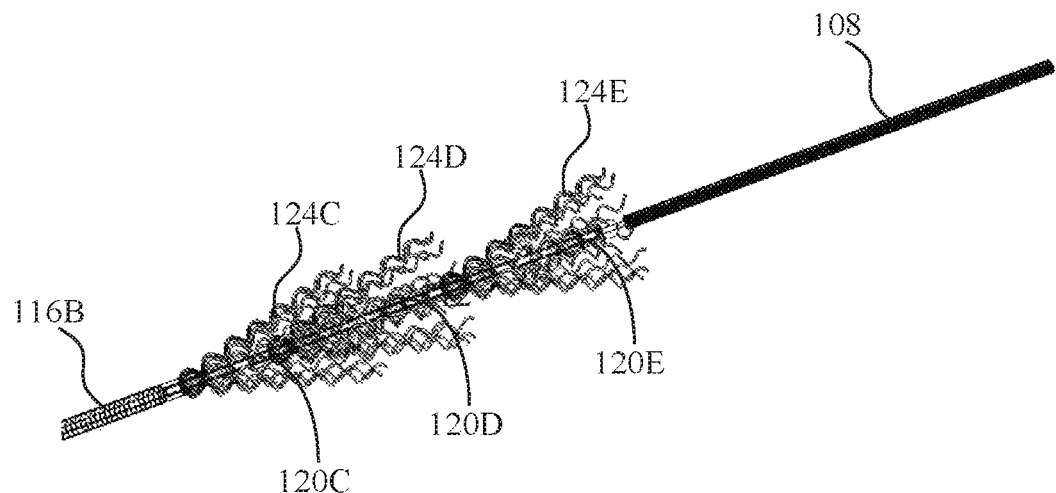
Figure 3C:
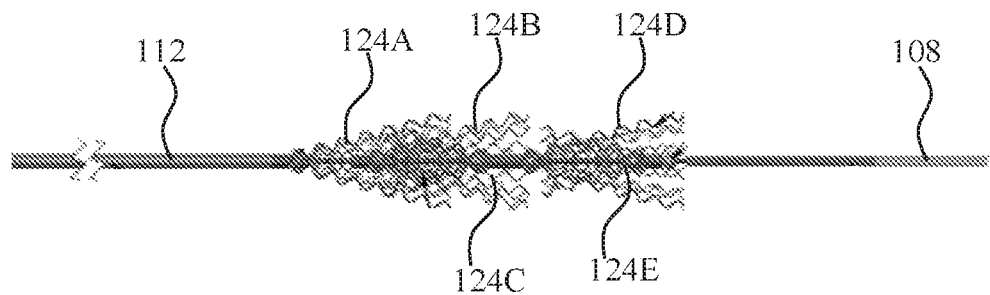

As can be seen in FIGS. 3B and 3C, more than one cylindrical body may be deployed in order to capture the clot. Deployment of several cylindrical bodies, either in the same opening direction (as seen in FIG. 3B) or in opposite directions (as seen in FIG. 3C) will cause formation of capturing cages assisting in capturing and retrieving larger clots or clot fragments. Deployment of several tubes may be carried out by additional pulling onto the deployment wire, such that after the deployment of the outmost distal tube, another pull of the wire will cause deployment of the more proximal tubes as force is being linearly transferred between the elements mounted onto the wire. Namely, once wire 106 is pulled on and cylindrical body 116E is deployed by tip tool 120E, another pull will cause cylindrical body 116D to proximate tip tool 120D (or if arranged differently, will cause tip tool 120D to proximate cylindrical body 116D), thereby causing the threads in cylindrical body 116D to unwind and deploy. Thus, by incremental pulling of the wire, the cylindrical bodies may be serially deployed.

Figure 4A:
FIG. 4A is a schematic representation of a grooved tube according to an embodiment of this disclosure.
Figure 4B:
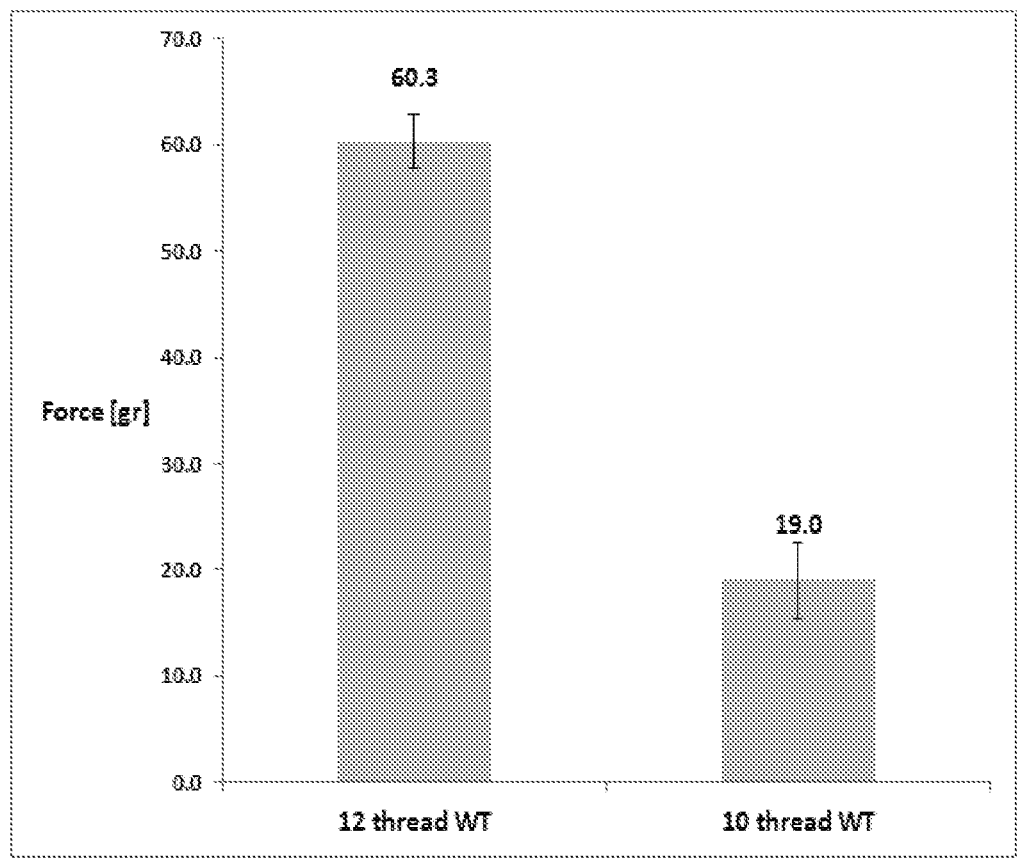
FIG. 4B shows the relation between the number of threads in the cylindrical body and the force required for deploying the threads.

Another control of the deployment sequence may be obtained by using tubes designed to deploy upon exertion of difference forces. For example, as can be seen in FIG. 4A, the tubes may be grooved by removing one or more of the threads. For example, as can be clearly seen in FIG. 4B, reduction in the number of threads results in less friction between the threads, requiring application of smaller forces to overcome the friction between the threads and cause their unwinding. Thus, pulling onto the wire at different forces will control the deployment of different tubes.

Once the cylindrical bodies are deployed, pulling the deployment wire will cause encaging of the clot. Generally speaking, in a first stage the cylindrical bodies are deployed such that the coiled threads unwind and anchor into the corpus. Pulling onto the deployment wire will cause deployed cylindrical bodies to proximate one another, resulting in initial compaction of the corpus. Upon further pulling, the unwound threads of adjacent cylindrical bodies will come into contact one with the other, at times causing entanglement of the threads, thus forming encaging of the captured corpus. Further proximation will increase compaction (thus decreasing the length of the device) to allow easier extraction of the device with reduced risks of corpus fragmentation. In a specific, non-limiting example, a combination of tubes having non-deployed lengths of 2.5 mm and 5 mm will eventually result in compaction of between 1.5-2 folds in length due to the proximation of the deployed tubes.

Further variation may be obtained by using tubes of various lengths, namely some of the tubes may have threads of a first length while other tubes may have threads of a second length. Such variation in length may also assist in improved entrapment of the clot, as deployed tubes having shorter threads may be compactly arranged within a deployed cylindrical body having longer threads, encaging the clot between the deployed cylindrical bodies in a compact manner. Such an arrangement is demonstrated in FIG. 3C, in which deployed cylindrical body 116E has shorter threads, while cylindrical body 116D have longer threads. As can be seen, proximation of cylindrical body 116D and cylindrical body 116E one to the other causes a hermetically closed cage in which a clot may be entrapped. This will also be demonstrated further below in connection with FIGS. 7B-9H.

Figure 4C:
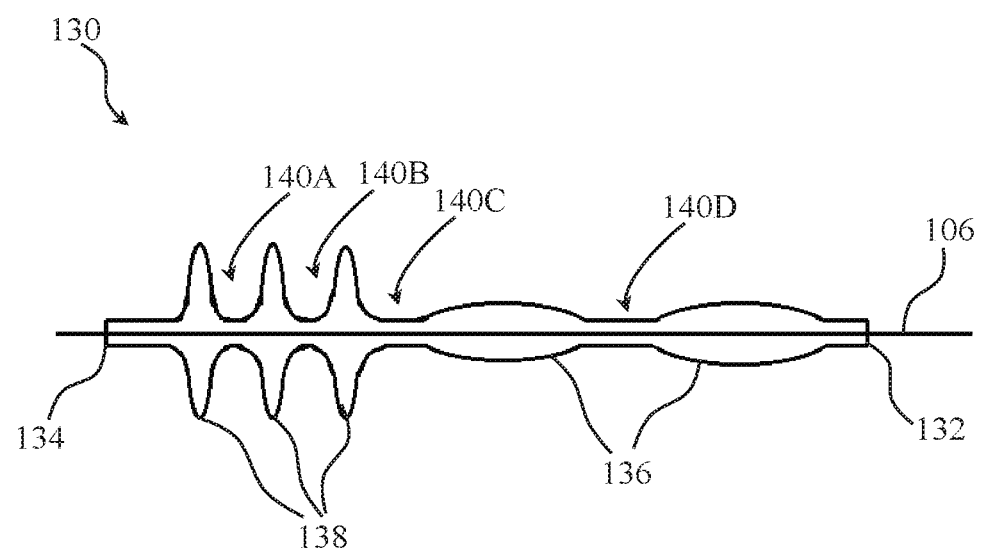
FIG. 4C is a schematic representation of a grooved, deployed closed tube.

As noted above, the corpus anchoring unit may comprise closed tubes, namely tubes having both ends closed and capable of radial expansion when force is applied by the tip tool onto one (or both) of the closed tube's ends. Such a tube is demonstrated in FIG. 4C, which schematically depicts a deployed, grooved, closed-tub 130. Tube 130 is associated with the deployment wire 106 and has a proximal end 132 and a distal end 134, at least one of which being associated with a tip tool (not shown). The wound coiled threads of tube 130 are fixedly attached to one another at both ends 132 and 134, such that when the tip tool applies a force onto one of the ends (resulting from pushing or pulling onto the deployment wire) the ends 132 and 134 proximate one another, causing reduction in length of tube 130 and radial expansion of the coiled threads between the two ends of the tube. In the example of FIG. 4C, some threads have been removed from the tube to form grooves 140A-140D, effectively dividing the tube into distinct sections, the number of threads removed determines the distance between the forms expanded sections of the tube, as well as the extent of radial extension of each section; for example, radially extended sections 138 are more radially extended as more threads have been removed as compared to radially extended sections 136.

As a man of the art may appreciate, although deployment of the device is the examples described herein is exemplified by pulling onto the deployment wire (i.e. displacing the wire to the proximal direction), deployment by pushing is also contemplated under similar linear movement and transition of force principles. Further, deployment by rotational movement of the wire, i.e. applying variable torque onto the different elements mounted onto the wire is also contemplated and within the scope of the present disclosure.

Figure 5A:
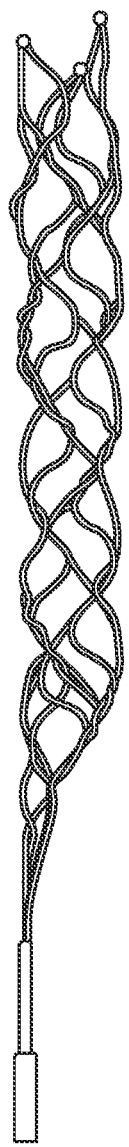
FIG. 5A shows a comparative thrombectomy device—Solitaire™, a commercially available revascularization device.
Figure 5B:
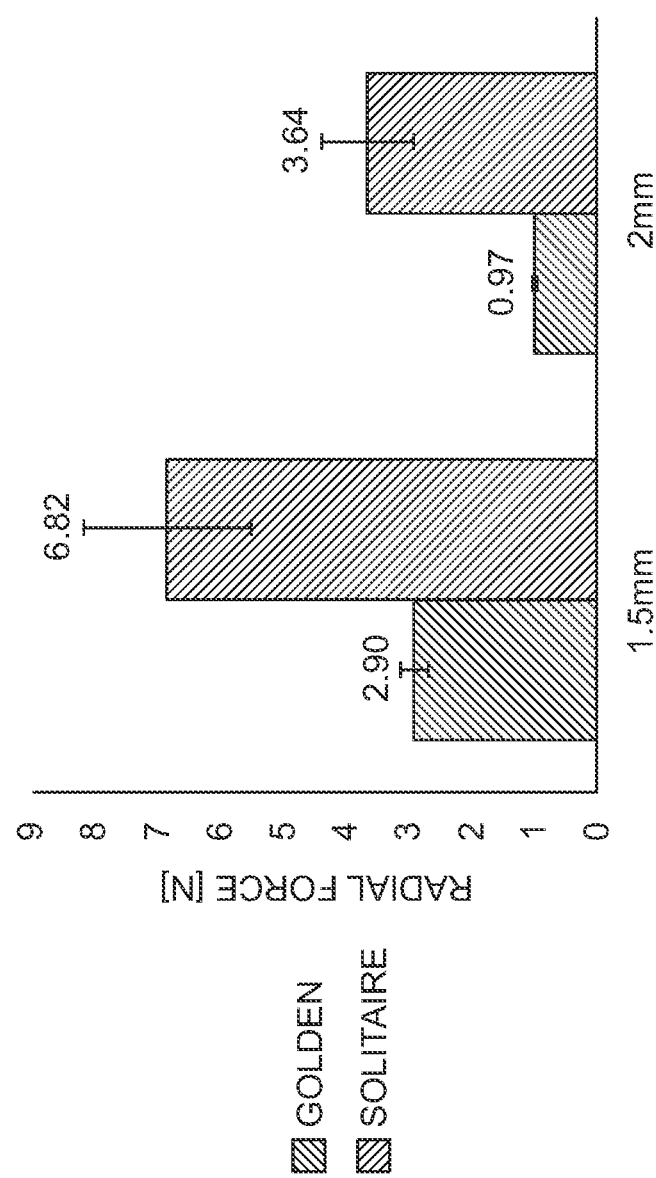
FIG. 5B shows a comparison between the radial forces applied by the device of this disclosure (named "golden" in this figure) and the Solitaire™ device.

As noted above, the device of this disclosure is designed as to exert minimal radial force on the inner walls of the blood vessels. This is obtained by the dimensions of the cylindrical bodies and its controlled deployment. FIG. 5B shows a comparative measurement of the radial force exerted on a blood vessel when a tube of the device of this disclosure is deployed, compared to the Solitaire™ device (the structure of which is seen in FIG. 5A). As clearly seen, the radial force exerted by the deployed threads of the device of this disclosure is significantly lower than the radial force exerted by the Solitaire™ device. It is of note that the cylindrical bodies of the unit of this disclosure are introduced into the blood vessel in a normally-closed configuration, controlled deployment is permitted by proper manipulation of the HMA and its associated deployment wire. This is contrary to the normally-open configuration of the comparative standard device (which is introduced into the blood vessel in a collapsed configuration that is maintained by a microcatheter; upon removal of the microcatheter the device automatically and immediately assumes its extended configuration).

At times, the device of this disclosure is configured to have dimensions that prevent the contact of the deployed cylindrical bodies (i.e. the unwound coiled threads) with the inner surface of the blood vessel. Meaning that in some embodiments, the cylindrical bodies of the unit are dimensioned such that one is the deployed state, the unwound coiled threads form a conical shape having a maximal diameter that is smaller than the inner diameter of the blood vessel.

Figure 6A:
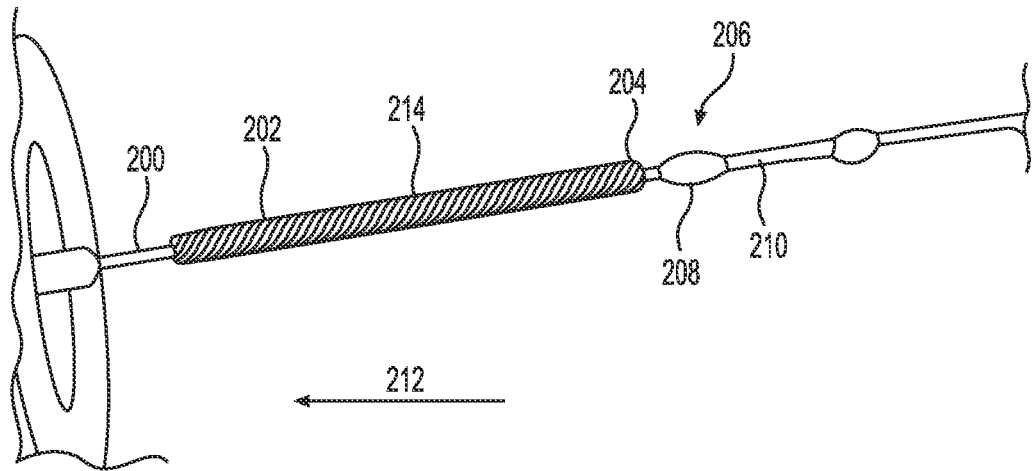
FIGS. 6A-6E show a step-by-step sequence of the engagement of the tip tool with the cylindrical body.

To better understand the engagement of the tip tool and the cylindrical body, reference is now made to FIGS. 6A-6E, which show the sequence of engagement of the tip tool with the cylindrical body. FIG. 6A provides an exemplary system, in which the deployment wire 200 is associated with at least one cylindrical body 202 and at least one tip tool 206 which is located at the cylindrical body's distal free end 204. The central portion of the cylindrical body 202 is enveloped by a polymeric sheet (for example a PTFE sheet) 214, the function of which will be described further below. The tip tool 202 comprises an ellipsoid main body 208 and a distal tubular element 210, the function of which will now be described.

Figure 6B:
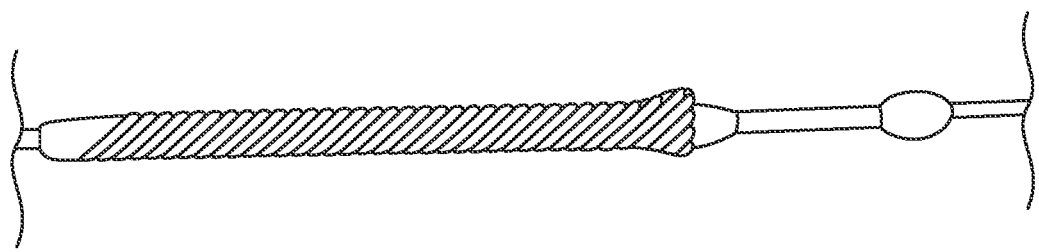
Figure 6C:
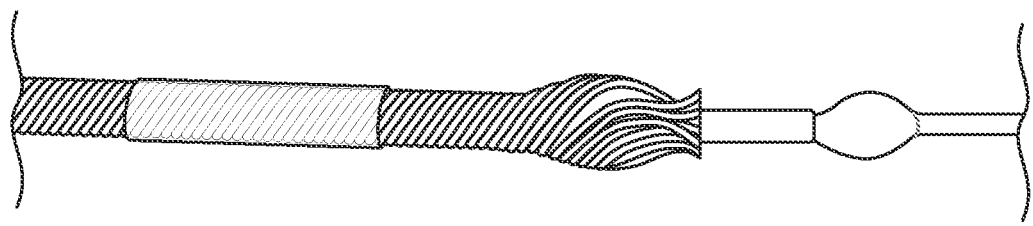

Once the deployment wire is displaced in the proximal direction (designated by arrow 212), i.e. the deployment wire is pulled, the ellipsoid section of the tip tool advances towards the distal, free end of the cylindrical body and engages the distal end, as seen in FIG. 6B. This engagement causes a primary unwinding of the wound threads, slightly separating the distal free ends of the wound threads one from the other. As the threads are made of a relatively flexible material (e.g. a flexible metal), further advancement of the ellipsoid portion of the tip tool causes elastic deformation of the wound threads, as seen in FIG. 6C, however, without further unwinding of the threads. Once the tip tool is further advanced in the proximal direction, the slightly separated edges of the wound threads engage the tubular element of the tip tool (FIG. 6C).

Figure 6D:
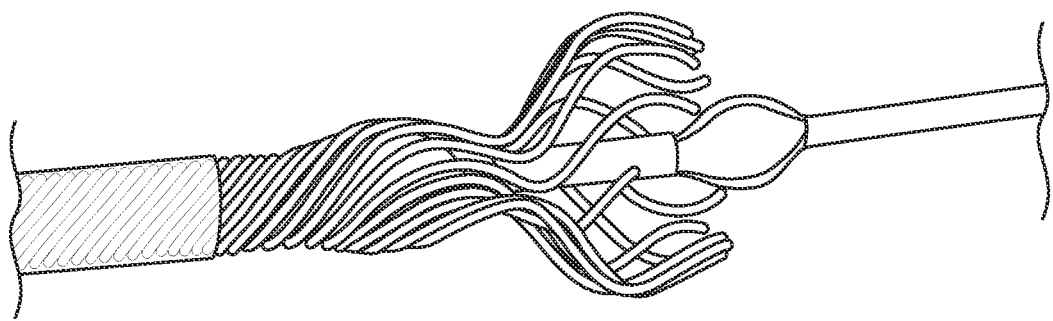
Figure 6E:
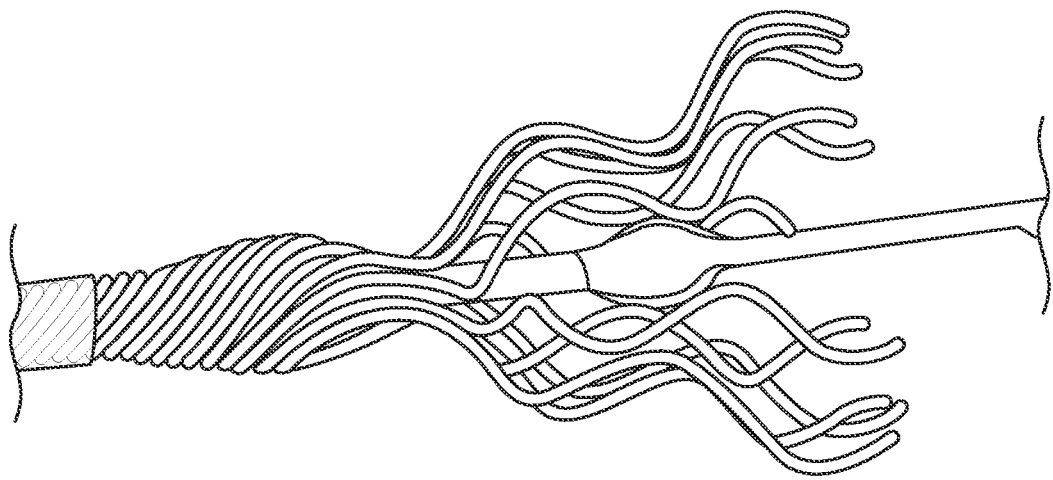

The dimensions of the ellipsoid portion and the tubular element are designed such that once the free edges of the wound threads engage the tubular element, such engagement causes the wound threads to unwind and flare-out into a deployed state, seen in FIG. 6D. Further advancing of the tip tool in the proximal direction, thus causes further unwinding of the threads from the cylindrical body (FIG. 6E). Thus, by controlling the angle of the impact of the edges of the wound threads with the tubular element of the tip tool, controlled deployment of the cylindrical body may be obtained.

As also seen in FIG. 6E, the polymeric layer 214 functions to limit the extent of deployment of the cylindrical body by limiting the length of operable section of the cylindrical body. It is to be understood that the device may or may not include such polymeric layers.

Figure 7:
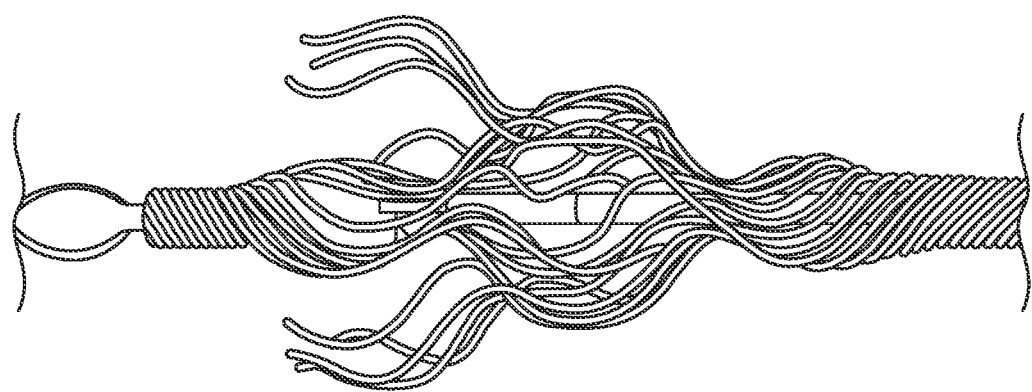
FIG. 7 show the formation of a cage structure between two cylindrical bodies opening to opposite directions.
Figure 8A:
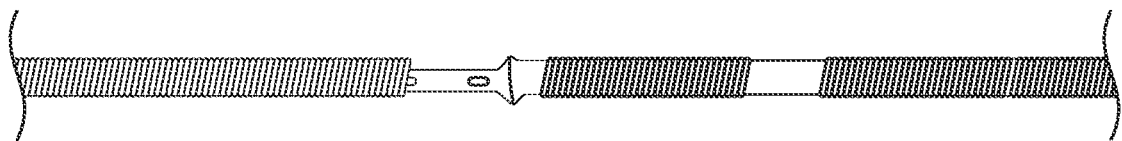
FIGS. 8A-8C show formation of cage structures formed by a plurality of cylindrical bodies that are not limited by a PTFE sleeve.
Figure 8B:
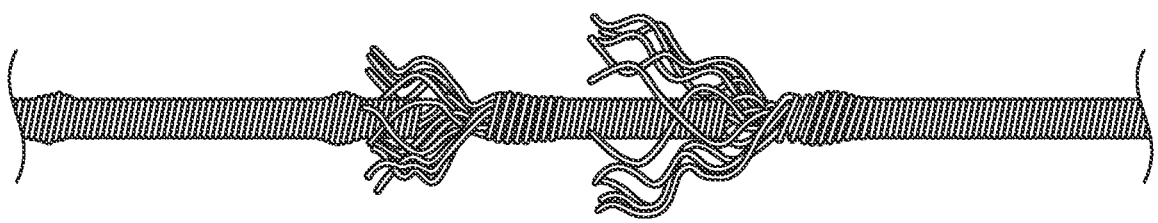
Figure 8C:
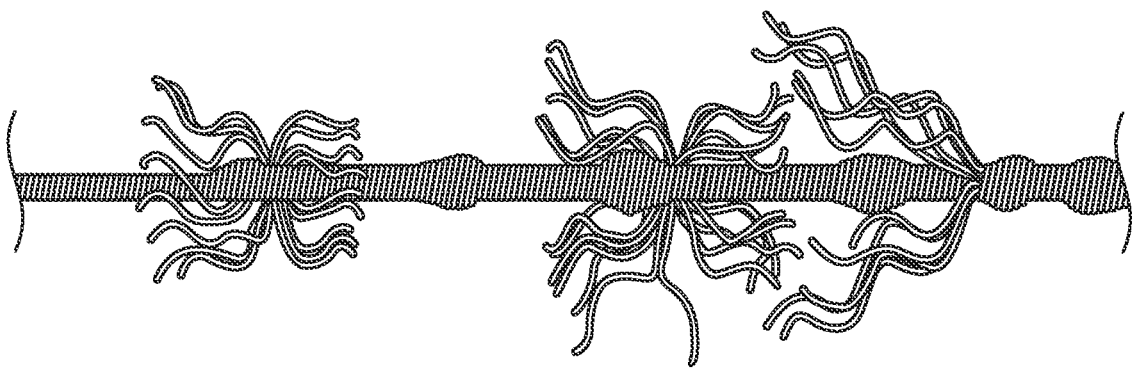
Figure 9A:
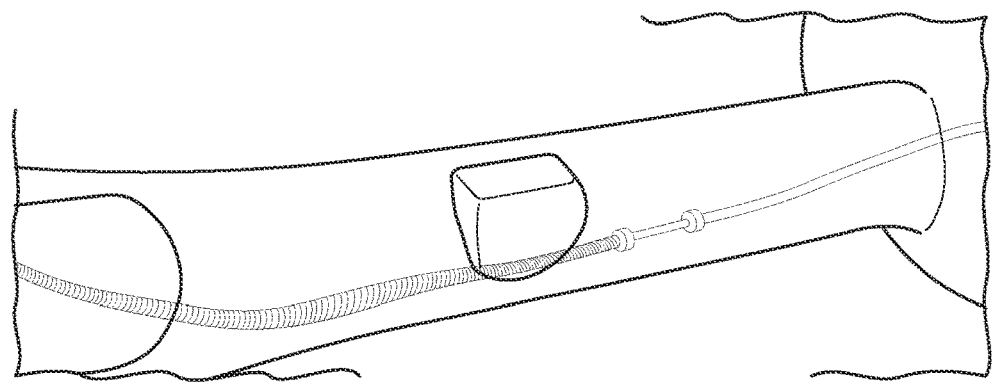
FIGS. 9A-9H show formation of cage structures formed by a plurality of cylindrical bodies that are limited by a PTFE sleeve so as to form a 2-step opening of the tubes.
Figure 9B:
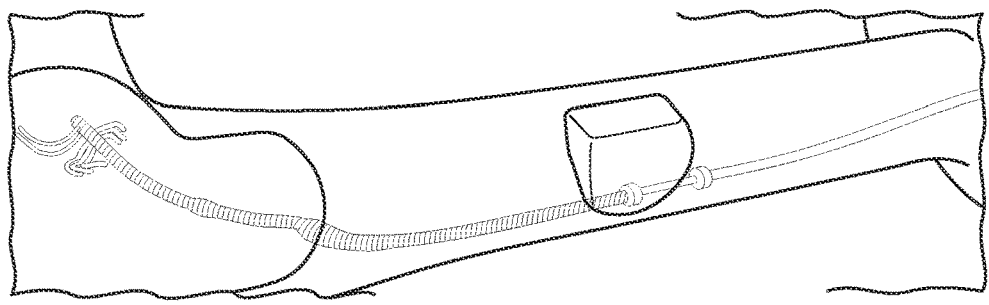
Figure 9C:
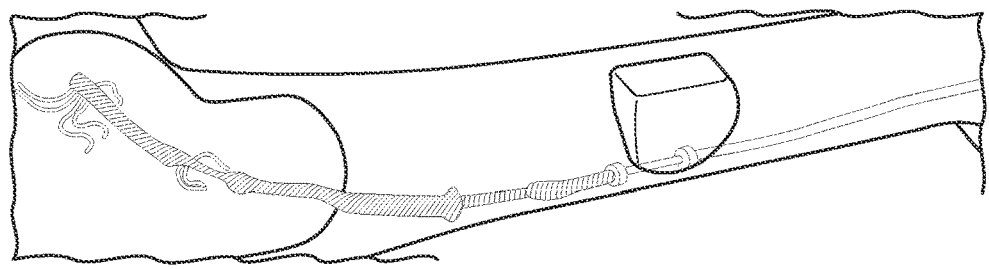
Figure 9D:
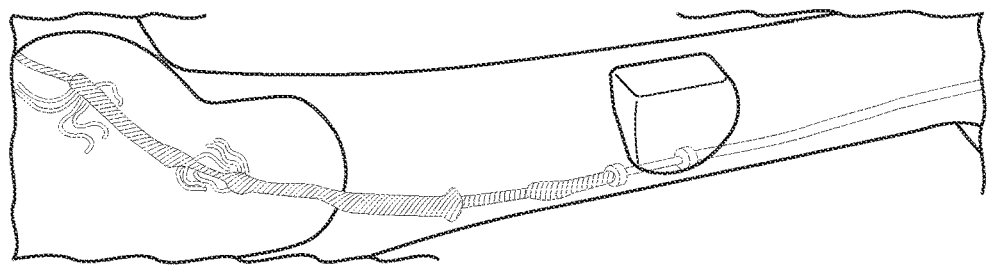
Figure 9E:
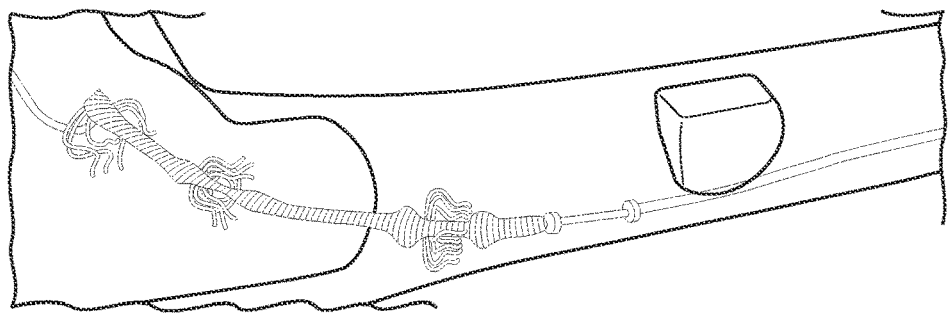
Figure 9F:
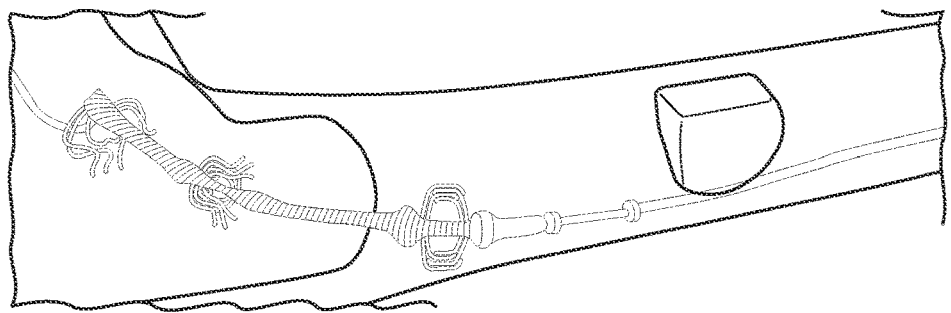
Figure 9G:
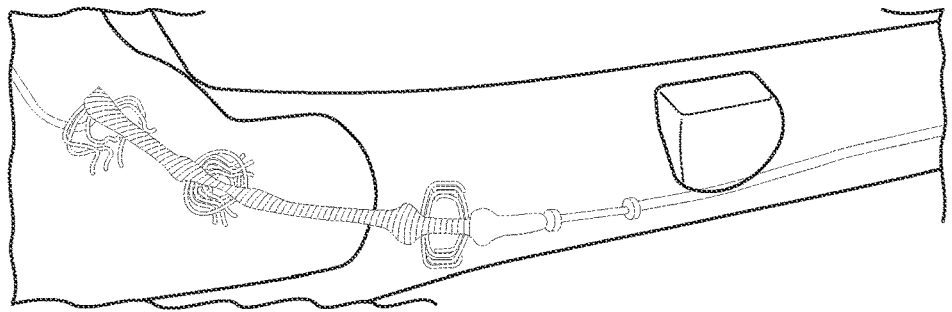
Figure 9H:
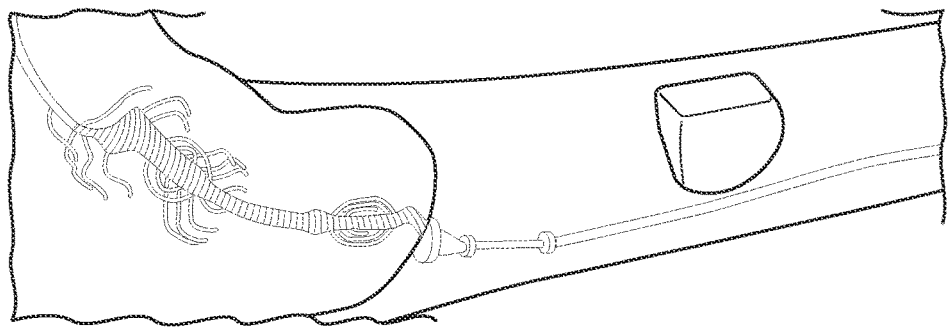

Seen in FIG. 7 is a system having at least one pair of oppositely oriented cylindrical bodies. The system of FIG. 7 comprises a proximal cylindrical body associated with a first tip tool at its distal free end, and a distal cylindrical body associated with a second tip toll as its proximal free end. Pulling the deployment wire in the direction of the arrow (i.e. in the proximal direction) causes the first tip tool to engage the distal end of the proximal cylindrical body, thereby causing its deployment. A further pull on the deployment wire causes the second cylindrical body to engage the second tip tool at the proximal end of the distal cylindrical body, thereby causing deployment of the distal cylindrical body. Once both cylindrical bodies are deployed, a further pull in the proximal direction causes them to proximate one another, thereby causing a cage-formation. It is of note that the shaft may also be rotated (i.e. torqued) in order to cause rotating movement of the deployed cylindrical bodies, thereby also causing the cylindrical bodies to proximate one another and concomitantly entangle their unwound coiled threads for better capturing of the blood clot.

The dimensions of the cylindrical bodies in the pair of oppositely oriented cylindrical bodies may be tailored, such that the unwound coiled threads of one of the deployed cylindrical bodies (typically the proximal cylindrical body of the pair) are longer than the unwound coiled threads of the other deployed cylindrical body (typically the distal cylindrical body of the pair). As the extraction of the device from the blood vessel is done by pulling the corpus anchoring unit in the proximal direction, such a design minimizes the contact of the unwound coiled threads of the distal cylindrical bodies with the inner surface of the blood vessel, thereby minimizing damage to the blood vessel.

The sequence of deployment of a system containing a plurality of such oppositely oriented pairs is shown in FIGS. 8A-9H. The cylindrical bodies of the system shown in FIGS. 8A-8C do not comprise a polymeric layer, and hence deployment of each cylindrical body is carried out to its full extent. Namely, each wound thread in each cylindrical body is deployed to its full operational length upon engagement with its corresponding tip tool (the most proximal tube is deployed first to its full extent, then the next-in-line distal cylindrical body is deployed to its full extent, then the next-in-line distal cylindrical body is opened to its full extent, and so on). After full deployment of the cylindrical bodies, proximation of the deployed bodies causes the formation of interlocked pairs of deployed bodies (i.e. primary cages). Upon further proximation, adjacent cages can form a further cage (i.e. secondary cage), etc. Each of such cages is anchored at a different section of the blood clot, and their proximation one to the other causes compaction of the blood clot for easier removal out of the vessel (as discussed further below).

In the exemplary system of FIGS. 8A-8H, each proximal cylindrical body in each pair of bodies is partially enveloped by a polymeric sheet, that limits the extent of deployment of these bodies. Thus, deployment of the device occurs in two stages. First, the all of the cylindrical bodies are partially deployed in a sequence along the deployment wire (starting from the most proximal and ending with the most distal along the wire) to a substantially similar unwound coiled threads length, i.e. to a thread length similar to the non-restricted bodies. It is, however, also possible to partially deploy all of the bodies simultaneously in the first deployment stage (not shown). After completion of the first stage, additional axial displacement of the deployment wire causes the restricted bodies to further deploy to a longer unwound coiled threads length in a second stage of deployment. Such a sequence of deployment divides the forces applied onto the blood clot during capturing, enable maintaining its integrity during capturing to minimize emboli.

Figure 10A:
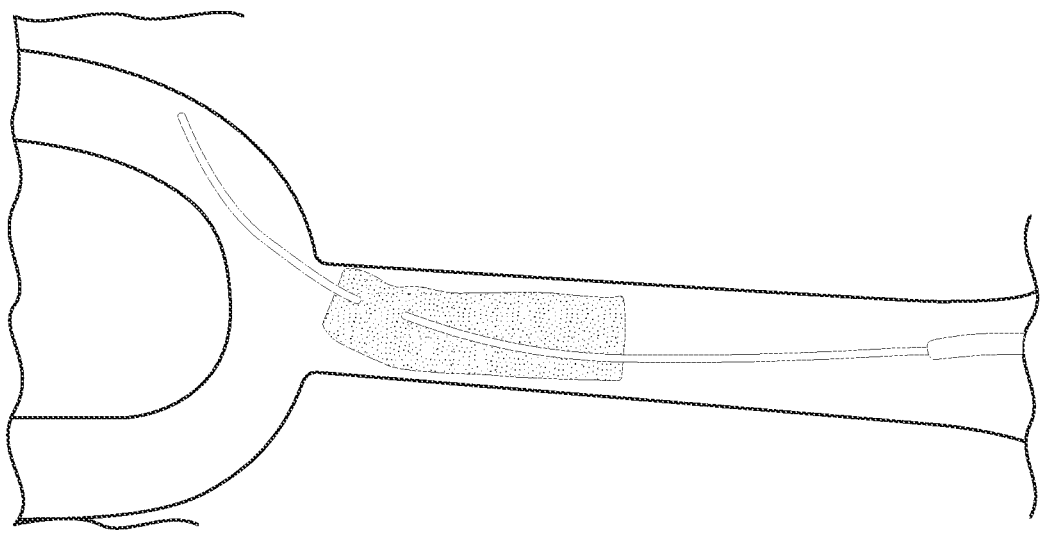
FIGS. 10A-10D show capturing of a simulated blood clot extraction, showing the deployed cylindrical bodies anchored into the blood clot, as well as the compaction of the blood clot during extraction as a result of the capturing.
Figure 10B:
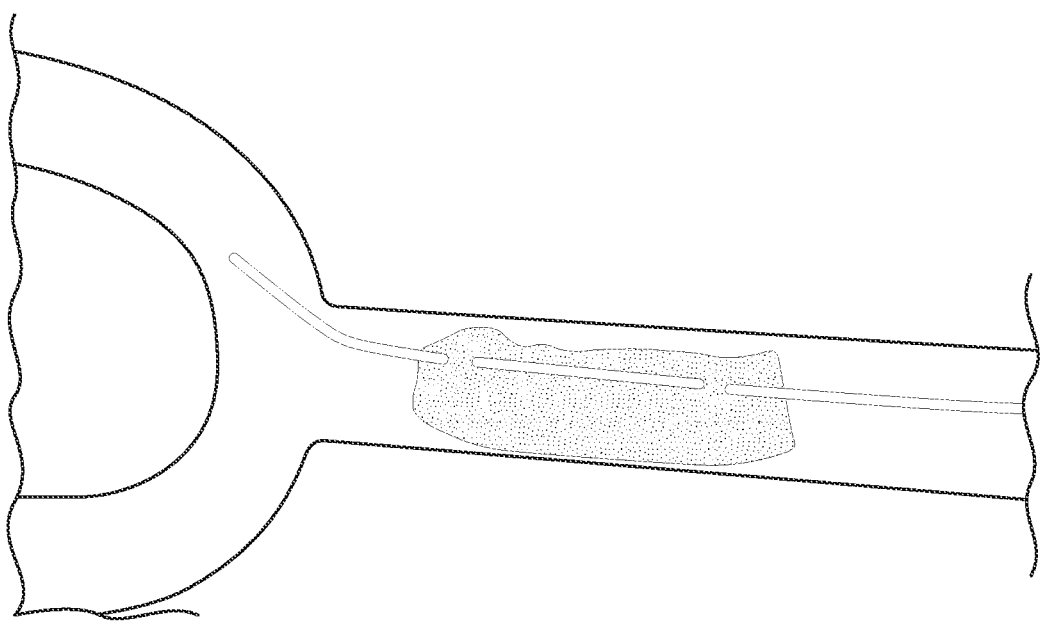
Figure 10C:
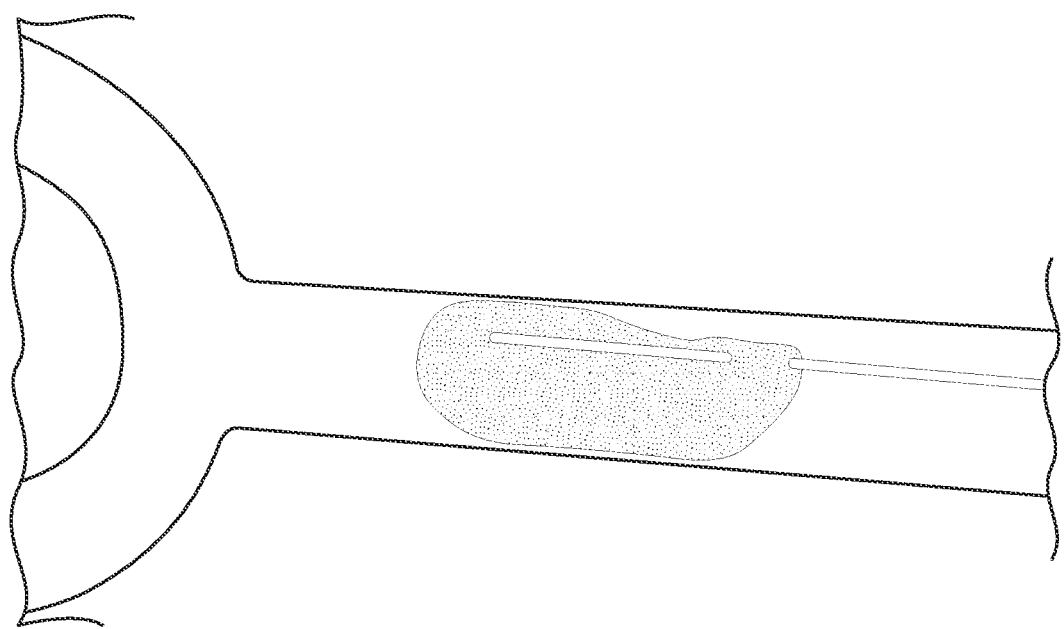
Figure 10D:
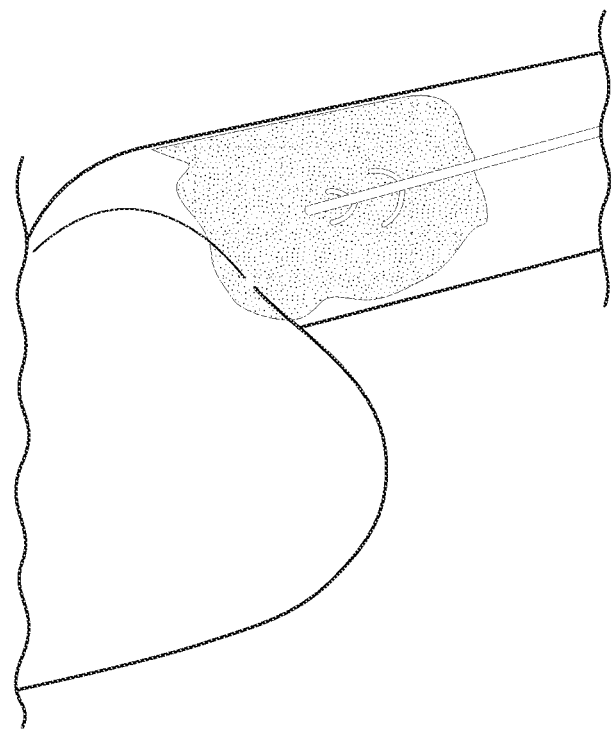
Figure 11A:
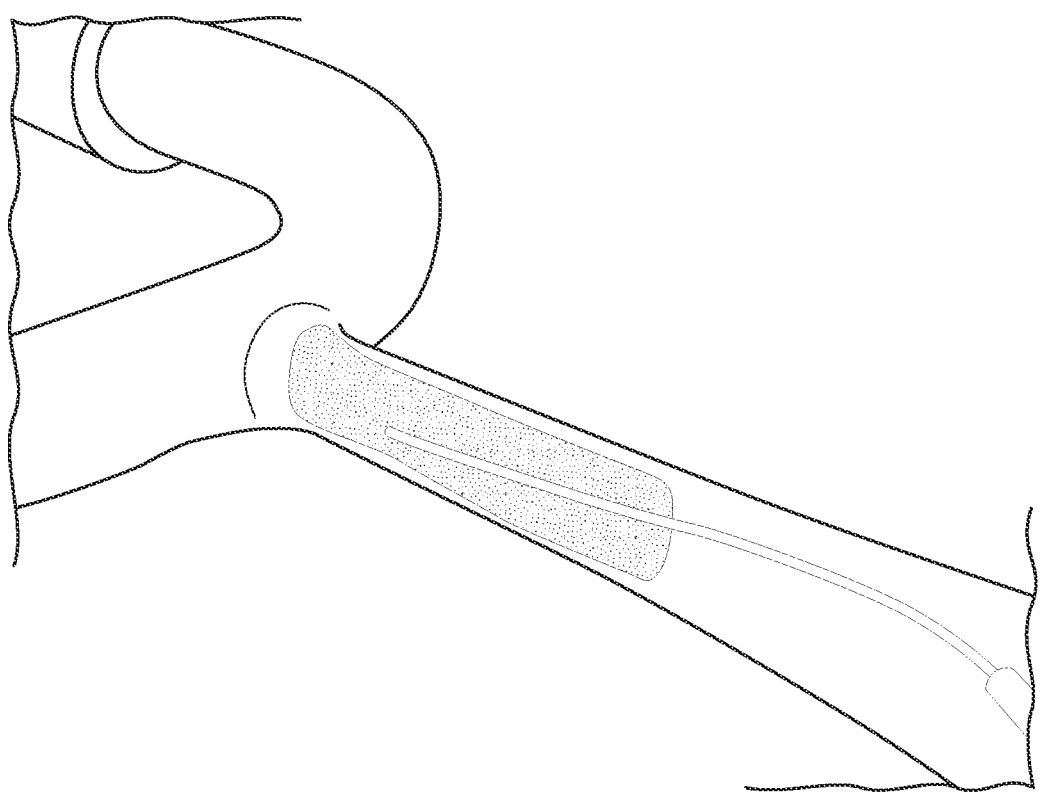
FIGS. 11A-11G show the maneuverability of the device within a simulated curved blood vessel. As can be seen, the blood clot is captured and retrieved without fragmentation.
Figure 11B:
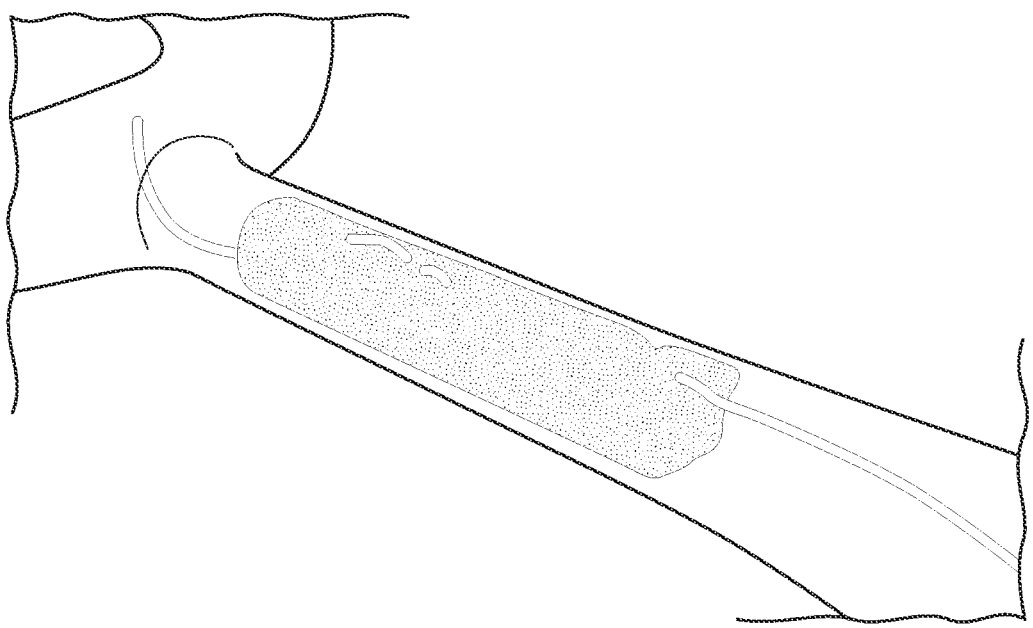
Figure 11C:
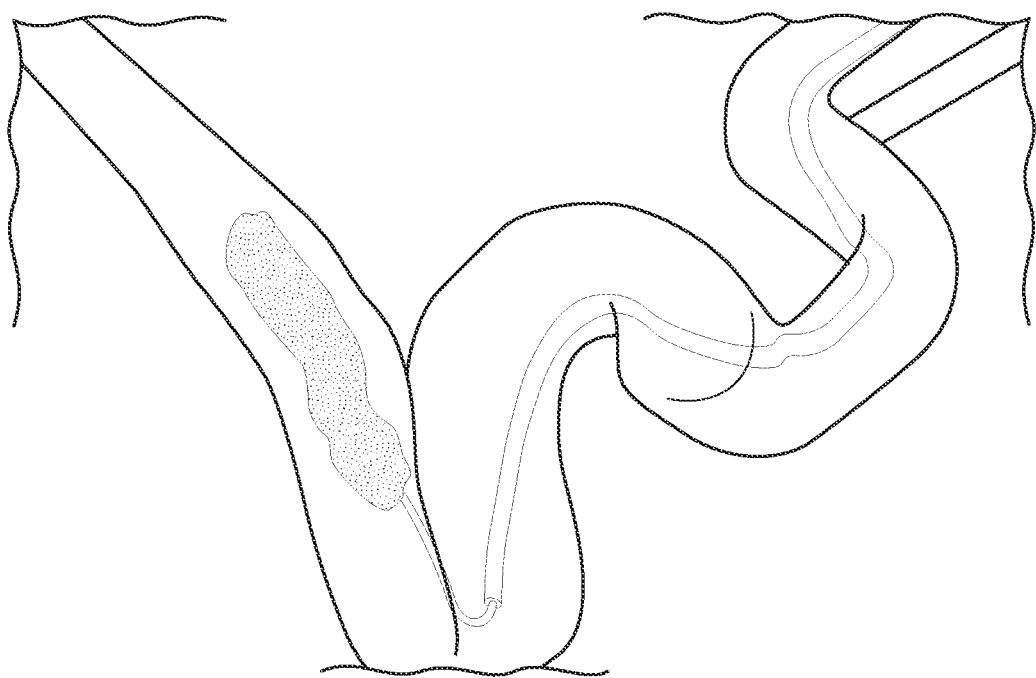
Figure 11D:
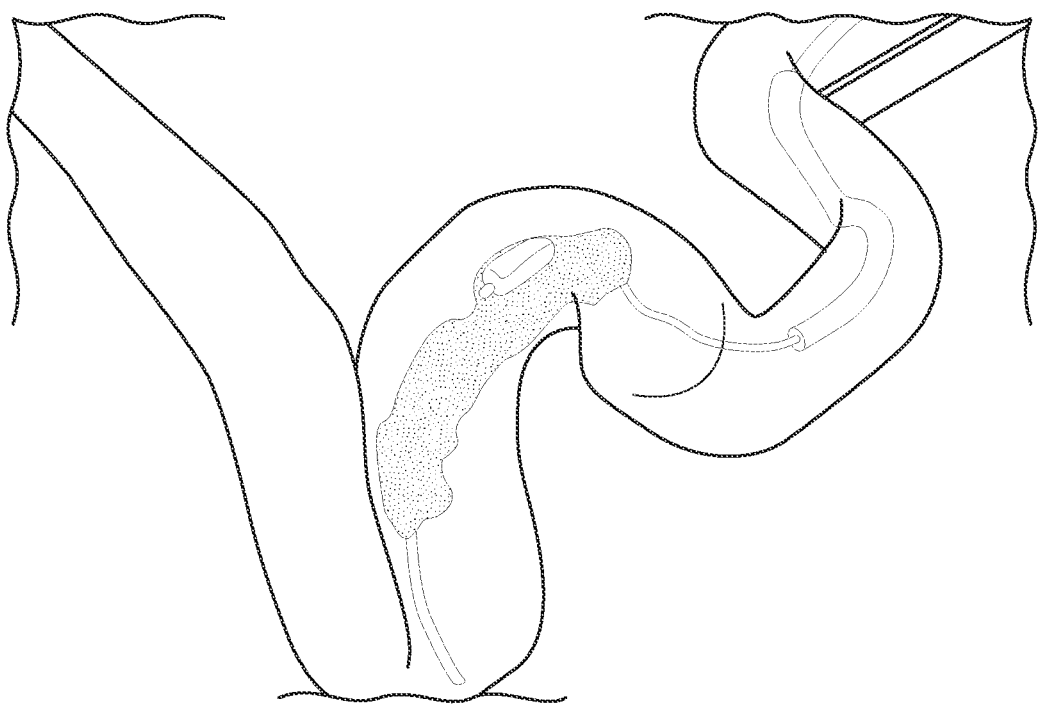
Figure 11E:
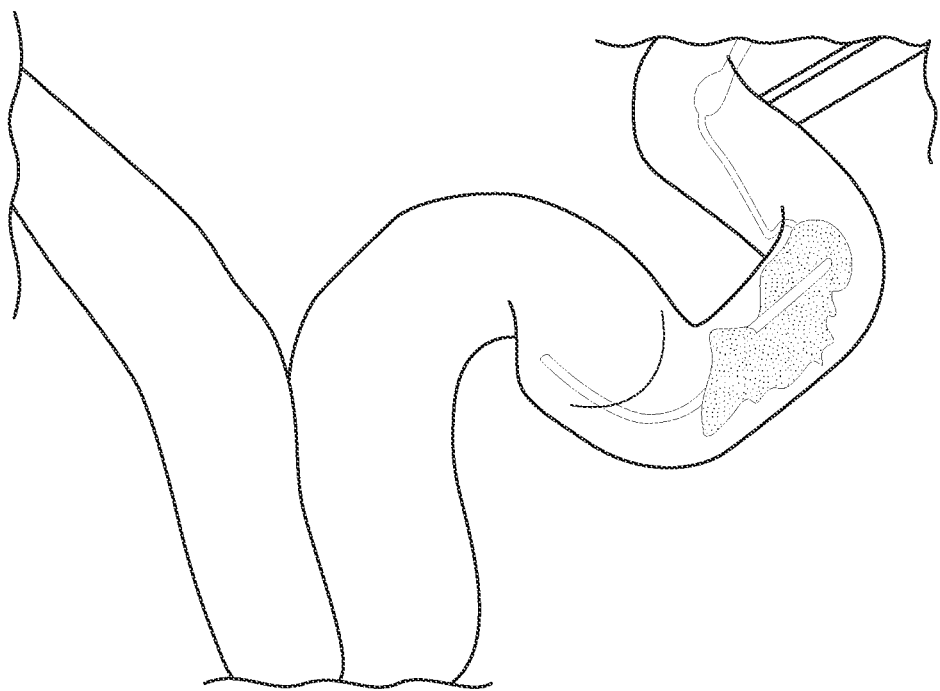
Figure 11F:
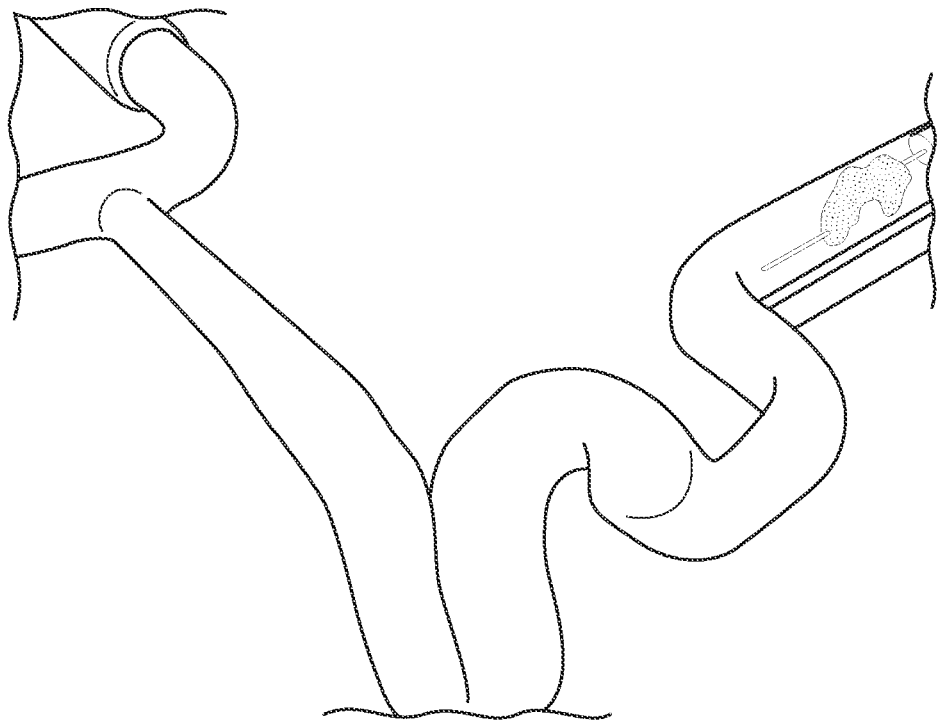
Figure 11G:
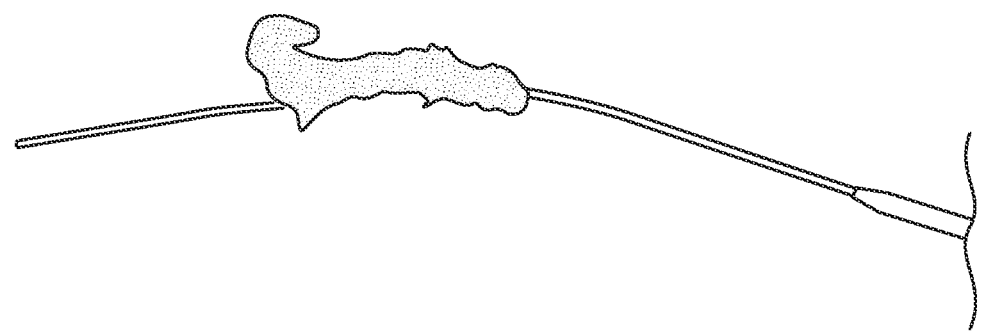

FIGS. 10A-10D show the capturing and retrieval of a simulated blood clot by a system of this disclosure. The system is first fully penetrated into the blood clot in a deployment state (FIG. 10A). Then the anchoring unit is operated and the various cylindrical bodies are deployed and anchored into the blood clot (as can best be seen in FIG. 10D). As evident from FIGS. 10A-10C, and as also explained above, the anchoring of the unit into the blood clot and the proximation of the deployed cylindrical bodies one to the other during the deployment and retrieval process, causes significant compaction of the blood clot, thereby further assisting its retrieval and further minimizes formation of emboli.

The ability of the system to maintain the captured blood clot integrity while maneuvering in complex and highly curved vessels is shown in FIGS. 11A-11G. In these figures, a step-by-step retrieval of a simulated blood clot is demonstrated, showing the flexibility of the corpus capturing unit while being maneuvered within a simulated blood vessel. No fragmentation or rupturing of the simulated blood clot was observed during the process and the clot was fully retrieved.

In Vivo Studies

All procedures were conducted according to international guidelines and were approved by the responsible local ethics committee.

Performance Study 1

The retrieval of blood clots from blood vessels was demonstrated in vivo, as follows. A 40 Kg swine was used in this study. Anesthesia was induced by an intramuscular injection of ketamine (35 mg/kg) and xylazine (5 mg/kg), and maintained with mechanical ventilation of oxygen with 1-2% isoflurane. Continuous monitoring of heart rate, respiration, oxygen saturation level (pulse oximetry), end tidal $CO_2$ and temperature allowed real time assessment of the physiologic status of the animal.

Common femoral artery access was subsequently obtained, and heparin bolus of 4,000 IU was intravenously administered. Anticoagulation was sustained with maintenance administration of 1,000 IU heparin every hour.

Thrombus preparation and application were done as previously described in [8]. In brief, thrombi were created by mixing 10-mL autologous blood of the animal with 1 gr barium sulfate (Sigma) and 0.25 mL bovine thrombin solution (Sigma). The mix was injected into a 4 mm inner diameter silicone tube, incubated for 1 hour at room temperature and cut into 10 mm length thrombi, which were injected into the target vessel. Due to the radiopacity gained by the added barium sulfate, the thrombi were visualized during angiography.

Figure 12:
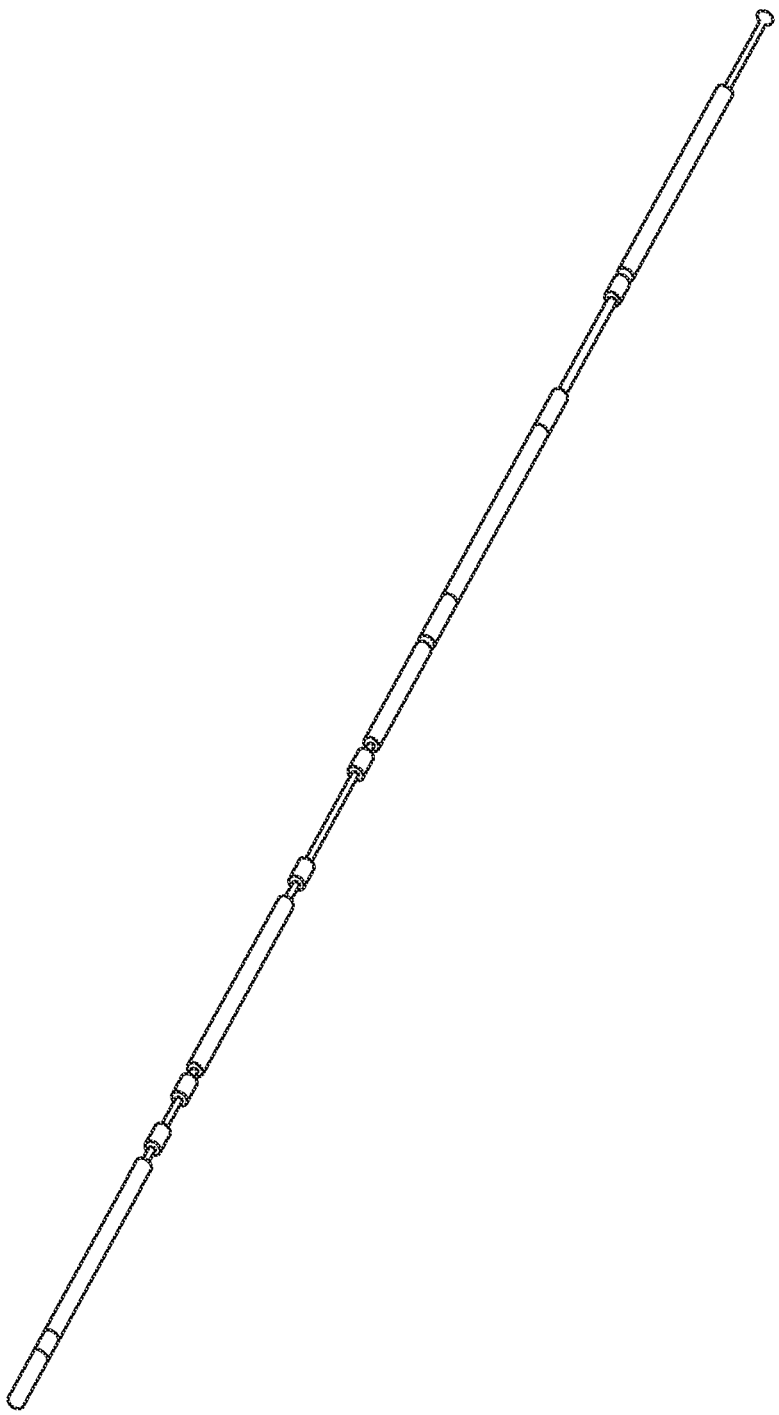
FIG. 12 is a perspective view of the device used in the animal tests described herein.
Figure 13A:
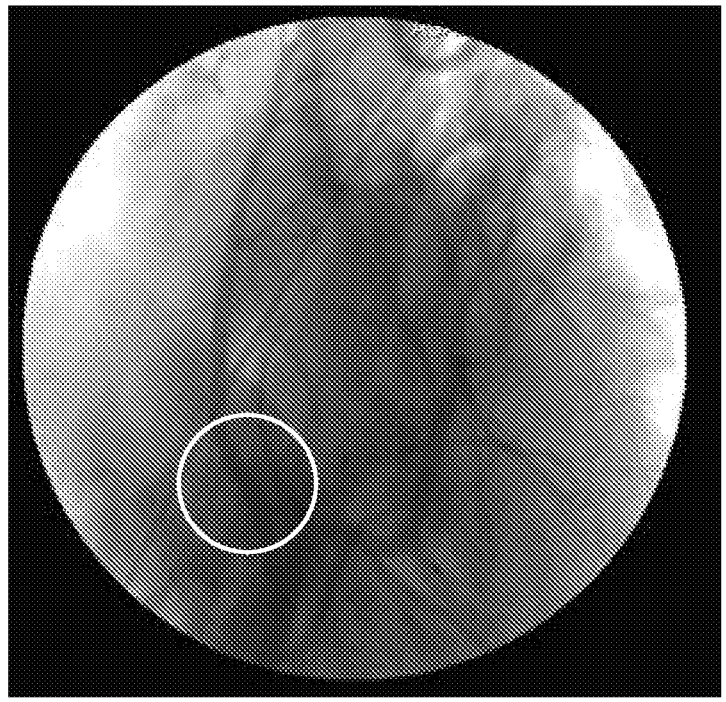
FIGS. 13A-13F show radiographic imaging (WC 128, WW: 256, zoom 117%) during animal test 1 (performance study 1), as follows.
Figure 13B:
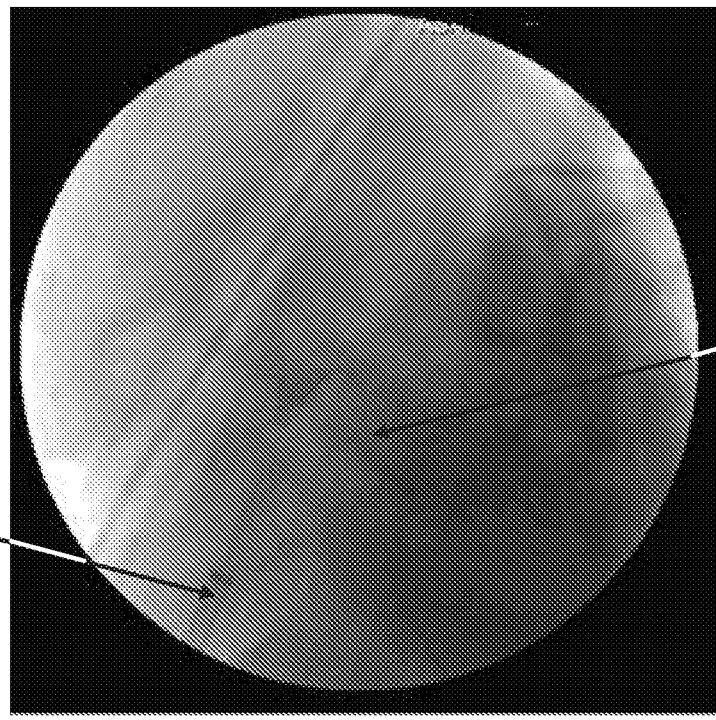
Figure 13C:
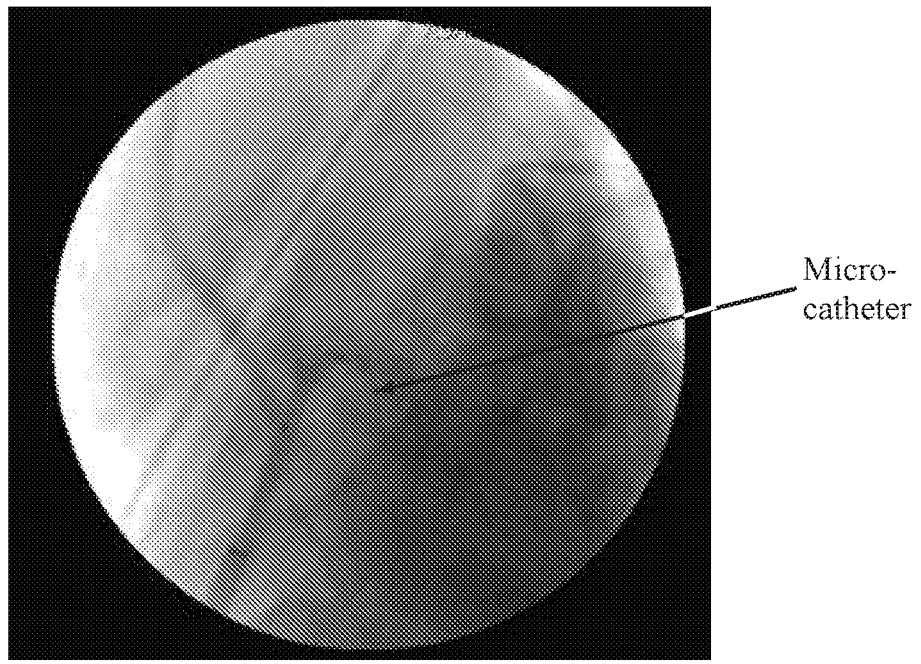
Figure 13D:
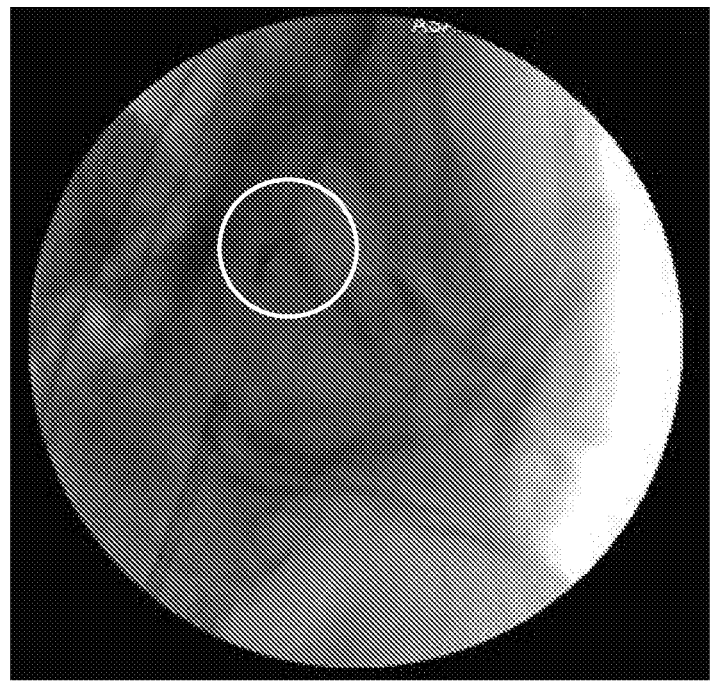
Figure 13E:
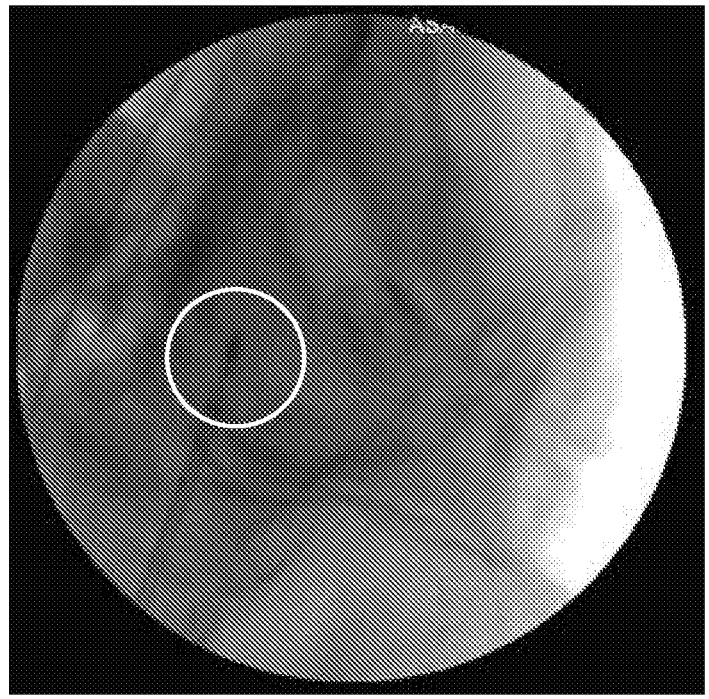
Figure 13F:
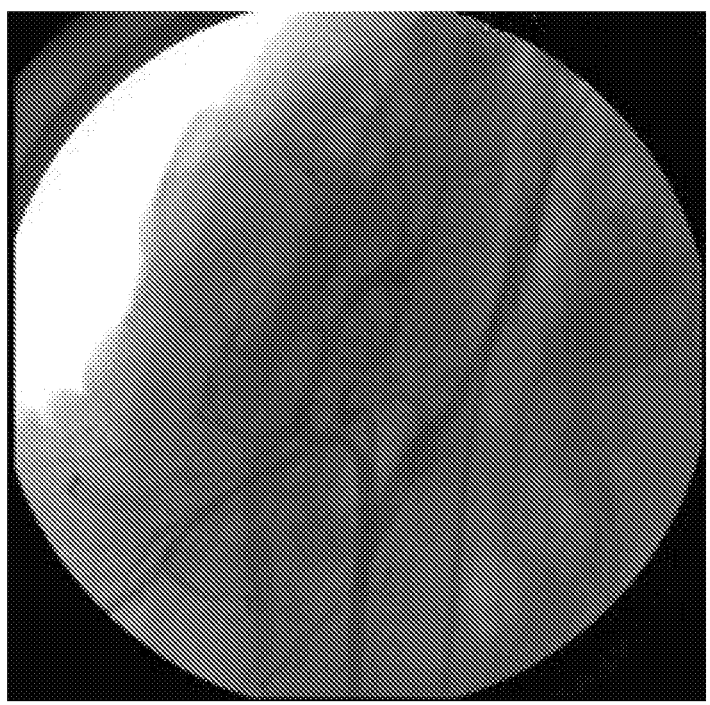
Figure 14A:
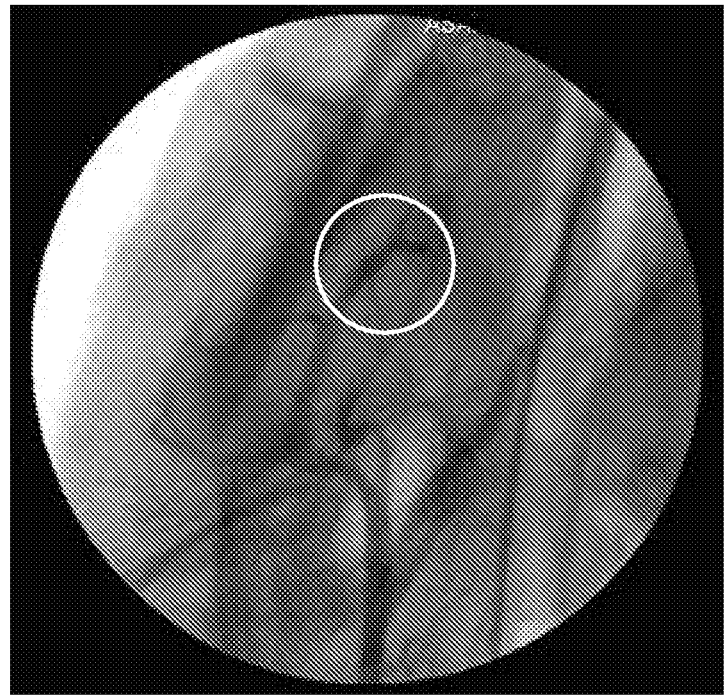
FIGS. 14A-14E show radiographic imaging (WC 128, WW: 256, zoom 117%) during animal test 2 (performance study 1), as follows.
Figure 14B:
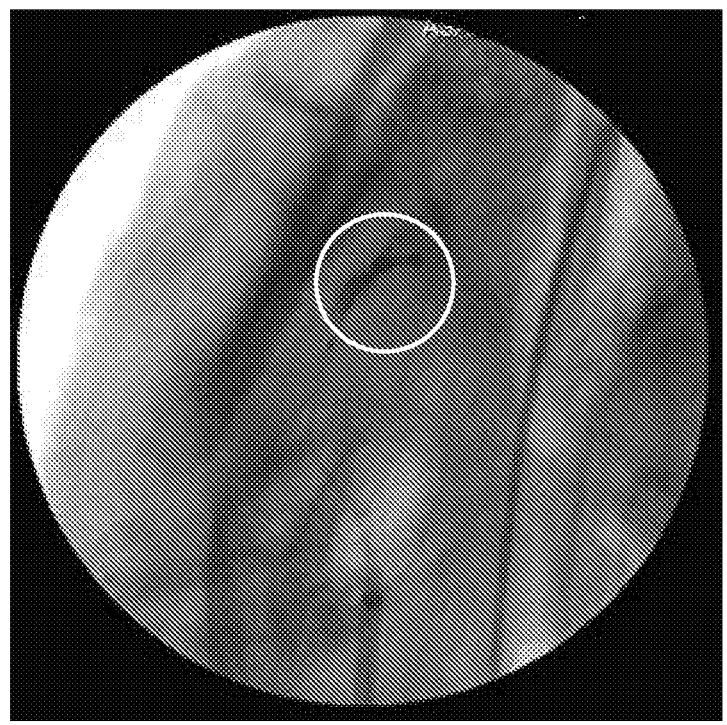
Figure 14C:
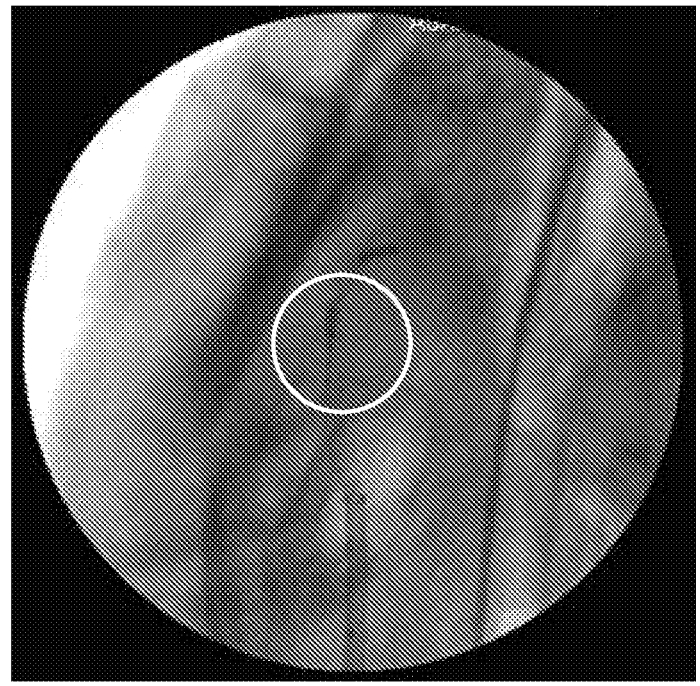
Figure 14D:
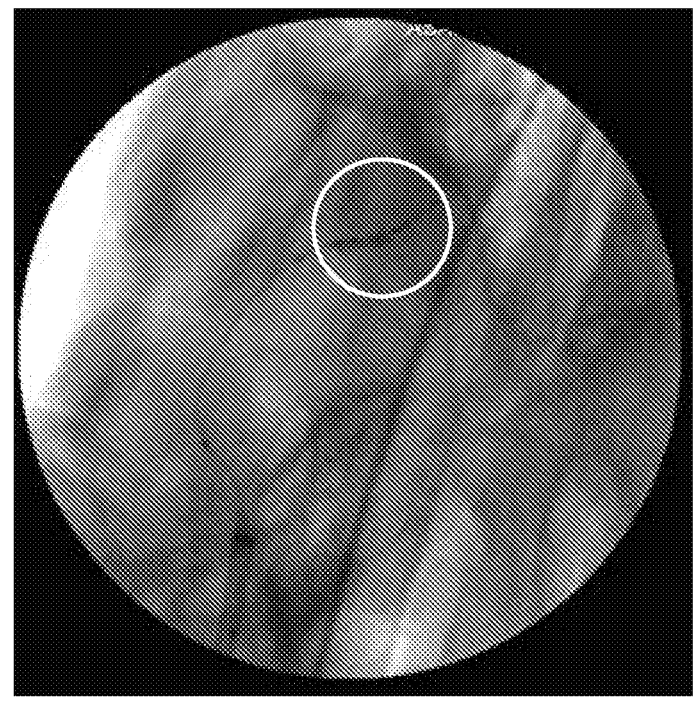
Figure 14E:
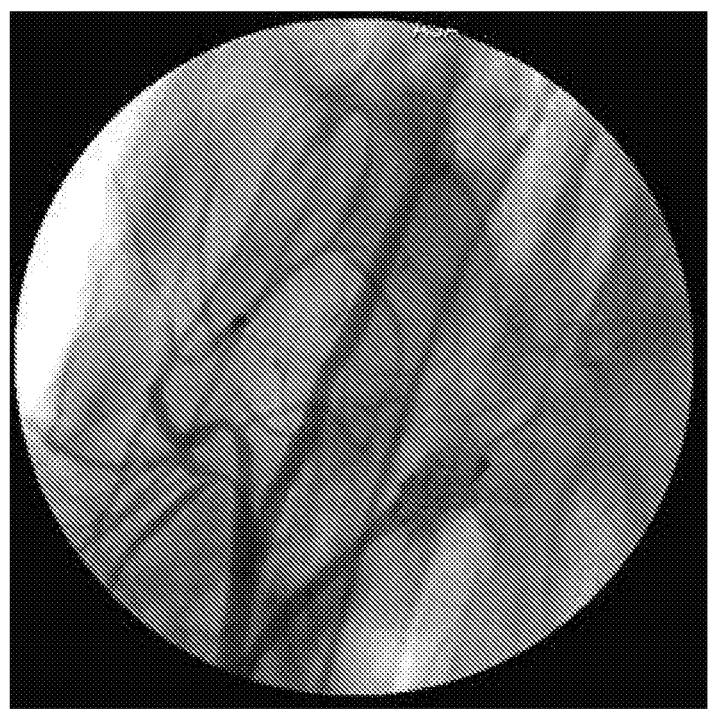

Device Configuration: the device configuration used in the animal study is demonstrated in FIG. 12. The device (corpus anchoring unit) included a stainless steel deployment wire (2000 mm, Ø 0.0045"), onto which five 12-strands tubes (OD 0.0136", ID 0.009"; strand Ø 0.0023") were mounted. The tubes were arranged according to Table 1 (along the proximal-distal axis). The open ends of the tubes were associated with tin tip tools, having a rounded configuration (OD 0.0082", ID 0.0067"); the tip tools contained Gold marker bands. The device was operated by an associated HMA (stopcock attached to a metal base or "guitar" handle).

TABLE 1

Arrangement of tubes in the device of FIG. 12

| | Tube 1 | Tube 2 | Tube 3 | Tube 4 | Tube 5 |
|---|---|---|---|---|---|
| Length | 5 mm | 5 mm | 3.5 mm | 5 mm | 5 mm |
| Open end | Distal | Distal | Proximal | Distal | Proximal |

Experimental Design and Angiographic Evaluation

The study was performed on a biplane angiography system. An 8F guiding catheter was inserted through the femoral artery access into the target vessel using a 0.014 inch wire. Selective occlusion of the internal maxillary artery and lingual artery was performed, which simulated the anatomic setting of an occlusion of the middle cerebral artery and the basilar artery in the human circulation.

Pre-formed thrombi were injected by a syringe into the guiding catheter and allowed to embolize distally into the swine internal maxillary and lingual arteries. The thrombi were allowed to mature in place for 10 min.

Vessel occlusion was confirmed by angiography and assessment of a Thrombolysis In Cerebral Infarction (TICI) flow grade of 0 or 1 (persistent occlusion or trickle flow). A 0.017" micro-catheter was navigated over the 0.014" wire across the occlusive thrombus. The wire was removed and contrast injection was performed to confirm endoluminal positioning distal to the occlusion.

The device of FIG. 12 was then advanced into the microcatheter and navigated to the occlusive thrombus, until the distal radiopaque marker of the device was observed in adjacent to the microcatheter end. Then the microcatheter was retrieved back. In order to ensure optimal positioning of the device, the device was repositioned in a way that either the three distal radiopaque markers of the device were positioned distal to the occlusive thrombus, or the first (i.e. proximal) radiopaque marker was positioned in adjacent to the proximal end of the occlusive thrombus.

Then the HMA was activated, initiating deployment of the device and engaging and trapping of the thrombus. During deployment of the device, the wire tubes of the device acted as trapping elements, creating closed geometrical cage-like shape designed to optimally trap the clot. In addition, the wire tubes were brought into proximity with one another (and in this instance compressed against each other), resulting in compression and entrapment of the occlusive thrombus.

As notes above, the formation of cages permitted a stable anchoring into the clots. The formation of primary cages between each pair of tubes followed by the formation of a secondary, larger cage between two proximating adjacent cages, further compacted the blood clot and enhanced the anchoring of the device for safe and effective removal of the clot.

After the occlusive thrombus was trapped within the deployed device, the microcatheter and the device were simultaneously pulled back into the guiding catheter under aspiration according to common practice.

Two cases of vessel occlusions were obtained. In both cases, the occlusive thrombus was extended into branches of the IMA artery. In test 1 (FIGS. 13A-13F), a single recanalization attempt was performed and flow restoration was achieved immediately after device deployment. In test 2 (FIGS. 14A-14E), a first recanalization attempt resulted in splitting of the thrombus into two portions, retrieving one portion of the occluding thrombus. Then, a second device was introduced and deployed, engaging the remaining portion of the occluding thrombus, and a full recanalization was achieved.

No distal thromboembolic events in the target vessel or in unaffected vessel areas occurred during passing of the thrombus, deployment, and retrieval of the device. Control angiographies showed no signs of vessel perforation, dissection, nor thrombus embolization or fragmentation or device fraction.

Performance Study 2

In this study, swine were considered the model for evaluation. The device of Animal Study 1 was tested for performance (i.e. clot trapping) by instrumentation of arterial segments similar to human indicated anatomies, with diameters ranging from 2-3.7 mm. The segments included: Brachial, Subclavian, Axillary, Internal Maxillary Artery and the External carotid arteries, as detailed in Table 2.

TABLE 2 tested swine arterial segments

| Procedure | Artery | Diameter (mm) |
|---|---|---|
| 1 | Internal maxillary | 3.0 |
| 2 | Left IMA | 3.5 |
| 3 | Brachial right | 3.6 |
| 4 | Brachial right | 3.1 |
| 5 | Brachial left | 3.7 |
| 6 | Subclavian left | 3.1-3.4 |
| 7 | Axillary left | 2.0 |
| 8 | Axillary left | 3.7 |
| 9 | Brachial left | 3.3 |
| 10 | IMA left | 3.2 |
| 11 | External carotid right | 3.4 |
| 12 | Brachial right | 3.7 |
| 13 | Externa carotid left | 3.6-3.7 |
| 14 | Axillary left | 1.6 |
| 15 | Axillary left | 2.0-2.1 |
| 16 | Brachial right | 2.0-3.0 |

The primary performance endpoint was re-canalization rate. Re-canalization rate was defined as successful capturing, trapping, and retrieval of thrombi as determined by angiographic evaluation (e.g., with TICI score ≥2 after thrombus retrieval in maximum 3 attempts).

The usability (mechanical performance) of the device was assessed on a scale of 1-5 (1=Poor, 5=Excellent), with respect to the following parameters:

Catheter navigation—Ability to navigate to a specific vessel that mimics intracranial setting in human: Insertion, navigation, pushability Device retraction (withdrawal)

Visibility of marker bands and tip

Handle activation\Deployment

Compatibility with commonly used catheterization tools (guide catheter, micro catheter, etc.)

User experience

Pre-procedural preparation: The animals were housed for three days prior to acute procedures. The animals were fed with commercial pellet food and water was administrated ad libitum. Each animal was examined for its general conditions, weight and health status, including Complete Blood Count (CBC).

Animals underwent overnight fasting period prior to procedure and an anesthesia according to animal laboratory standard procedure. Induction: Animals were induced by an IM injection of Telazol (4.4 mg/kg) mixed with xylazine (2.2 mg/kg). Atropine (0.05 mg/kg) was delivered intramuscularly as a premedication following induction. Maintenance was obtained by administration of 1-3% isoflurane via endotracheal tube (mechanical ventilation). Heparin was administered with a goal activated coagulation time (ACT) between 250 and 300 seconds. Vital signs were monitored following induction of general anesthesia; E.C.G., HR, SpO2, capillary refill time and Temp The blood clots for the thromboembolization process were prepared by using a 20 ml whole blood obtained into a syringe, mixed with 2 g barium sulfate powder in a gentile rotational movement. The mixture was incubated in the syringe at room temperature for 120 minutes until it showed a multiply-layered structure of blood constituent and barium. After the sedimentation, the solid component was separated from the serum component and a small piece of clot was carefully resected, measuring approximately 5 mm in diameter and 10-20 mm in length, from the aforementioned solid component with both fibrin-rich and erythrocyte-rich layers. Finally, each prepared thrombus was filled into a silicone tube with saline for reservation until injection.

Surgical procedure: After groin opening (femoral) and insertion of an 8/9F sheath, a balloon GC 8F was advanced over the wire (0.035" wire). Road mapping of the target vascular bed and selection of target vessels. The pre-prepared clot was injected to the pre-selected target vessel and left for embedding for at least 10 min prior deployment. Selective pretreatment angiography was performed in order to check that no vascular damage was caused by the clot insertion procedure: TICI scoring was evaluated to record perfusion rate. Vessel dissection or perforation, thromboembolic event and clot fragmentation were checked for during this evaluation.

Thrombectomy procedure: the following procedure was carried out for every treated vessel segment:
1. An 8F balloon GC was positioned as close as possible to the position of thrombus employing a standard method.
2. A micro-catheter of 0.017" or 0.021" ID was advanced crossing the clot, over a 0.014" or 0.016" guide wire.
3. The guide wire was retrieved
4. The device was removed from its packaging and inspected before insertion.
5. The device was advanced through the micro-catheter till the distal tip was angiograpically observed at the microcatheter distal end. The device was positioned relatively to the clot so that the device proximal marker was at the clot proximal edge
6. The micro-catheter was retracted
7. Repositioning of the device relatively to the clot (if necessary): device proximal marker at the clot proximal edge
8. Opening of the device (actuation of the corpus-anchoring units) was performed after releasing the handle safety catch, by sliding the handle activator, to enable device deployment and clot engagement and trapping. It was verified that the radiopaque markers moved toward each other.
9. The balloon GC was inflated and vessel sealing verified.
10. The device was retracted with the micro-catheter as one unit into the balloon GC, while aspirating by applying negative pressure when retraction started The balloon GC was deflated.
11. Retrieved/captured clots were observed and photographed and visual inspection of device integrity was performed.
12. Angiographic assessment with TICI and vessel integrity (e.g., dissection/perforation), vasospasm scoring was performed After each retrieval attempt, the vessel was examined for remaining and additional occlusions (i.e. part of the clot that remained in place, distal emboli and affected new territories). In case the clot was located in a bifurcation, occluding 2 branches of the vessel, only the main branch was treated. The procedure was considered successful when the main branch underwent recanalization (with TICI score ≥2)

In case of failed trapping, or partial success in clot retrieval, the device was withdrawn for an additional deployment, the device was cut in the distal shaft coil proximal to the activation area in order to be released from the micro-catheter, the MC integrity was verified for additional use and a new device was inserted. The advancement to the occluded segment, engagement/trapping and aspiration steps were repeated. Up to 3 attempts (3 devices) were allowed for a procedure to be considered successful.

Animal euthanasia and sacrifice was performed by IV bolus injection of an over dose of sodium pentobarbital (100 mg/kg) while the animal is under general anesthesia.

Results 15 clots were treated with no vessel perforation or dissection after insertion of the clot and device. Out of the 15 clots, 14 were successfully retrieved with post thrombectomy recanalization TICI score of 2 or higher that was retrieved in 3 attempts or less, as detailed in Table 3. Table 4 summarizes the segmentation of the number of attempts for the 14 successful procedures.

TABLE 3 re-canalization assessment (TICI scores) after procedure

| | TICI score | | | |
| --- | --- | --- | --- | --- |
| | 2a | 2b | 3 | Fail (0 or 1) |
| # of clots | 0 | 10 | 4 | 1 |

TABLE 4 number of attempts

| | Number of attempts | | | |
| --- | --- | --- | --- | --- |
| | 1 | 2 | 3 | Average |
| # of clots retrieved | 12 | 1 | 1 | 1.2 ± 0.56 |

As evident from Table 3, 93.3% of the procedures ended with successful retrieval (based on the success criterion of TICI ≥2 with a maximum of three attempts) and good recanalization scores.

In terms of number of attempts, as detailed in Table 4, 12 out of the 14 (i.e. 85.7%) successful retrievals were achieved within the first attempt. No distal occlusions or affected new territories were documented in the study.

Mechanical performance (usability) evaluation was assessed in a scoring grade on a 1 to 5 scale (1—Poor, 2—Mediocre, 3—Fair, 4—Good, 5—Excellent). Table 6 provides a summary of the mechanical performance scoring.

TABLE 6 mechanical performance evaluation

|  | Score | | | | | Average | |
| --- | --- | --- | --- | --- | --- | --- | --- |
|  | 1 | 2 | 3 | 4 | 5 | score | STD |
| Catheter navigation - Ability to navigate to a specific vessel that mimics intracranial setting in human: insertion, navigation, pushability | 0 | 0 | 0 | 0 | 15 | 5 | 0 |
| Device retraction (withdrawal) | 1 | 0 | 0 | 2 | 12 | 4.6 | 1 |
| Visibility of markers and tip | 0 | 0 | 0 | 0 | 15 | 5 | 0 |
| Handle activation\Deployment | 0 | 0 | 1 | 0 | 14 | 4.9 | 0.5 |
| Compatibility with commonly used catheterization tools (Guide catheter, micro catheter, etc.) | 0 | 0 | 1 | 0 | 14 | 4.9 | 0.5 |
| User experience | 0 | 0 | 1 | 0 | 14 | 4.9 | 0.5 |

Visual inspection under light microscope with magnification ≥30× was performed to all devices that were used in the study. All devices were intact, no kinks/breaks or other damages were observed in any of the devices.

Safety 4 crossbred domestic female swine weighting 40-50 Kg (approximately aged 3-4 Mo) were used. The device was tested for safety by simulated instrumentation of arterial segments (considered the test system) with diameters ranging from 2-5.5 mm and with similar anatomy to humans. The following vessels were used: Subclavian, Axillary, common Carotid, Femoral and Saphenous.

Pre-procedural preparation: Each animal was examined for its general condition, weight and health status, including Complete Blood Count (CBC). Animals were put in quarantine for a period of 3 days for acclimation purposes, and had a 12 hours fasting period prior to index procedure. Anesthesia was performed according to the animal laboratory standard procedure. Once an appropriate level of sedation was induced, the animal was intubated with an endotracheal tube (dependent on the size of animal). The animal was connected to the anesthesia machine where isoflurane gas was used to maintain a surgical plane of anesthesia. Mechanical ventilation was provided. IV Heparin Loading dose of 100-150 IU/kg was administered and ACT was monitored throughout the procedure. Heparin was administered IV when ACT levels were ≤250 sec. Following induction of general anesthesia, E.C.G., HR, SpO2 and temperature were monitored. Blood was collected for CBC and chemistry.

Surgical procedure: angiography was performed before, during, and after each simulated thrombectomy procedure, for segment selection (according to diameter, angle of the vessels, side branched and tortuosity) and evaluation during and after the procedure. Vessel registration was performed based on anatomical landmarks and specified in the angiograms.

Catheterization was performed according to the following procedure: angiographic road mapping were performed as per common clinical practice: Entry artery (groin) puncturing for arterial access. Insertion of an 8F or 9F vascular sheath to access artery, followed by insertion of a 0.035" Guidewire (GW). Advancement (Over the Wire, OTW) of a 6F/8F Guide Catheter (GC) and Road mapping of the target vascular bed.

Thrombectomy procedure: The thrombectomy procedure was carried out as described above in Performance Study 2, including angiographic assessment with TICI and vasospasm scoring. Final angiographic evaluation included angiographic evaluation and scoring for eventual vessel dissection or perforation, vasospasm, thromboembolic event. End of catheterization procedure with closure of entry groin till hemostasis was reached.

Follow-up assessment: Animals were assessed daily for general health conditions (e.g. Animal injuries and visual infections, presence or absence of feces, bleeding and food intake). Animal weight was also followed. No adjuvant post procedure therapy was indicated in these animal procedure. Post procedure preventive antibacterial therapy with antibiotics was given for 5 days post-surgery.

Prior to sacrifice, animal underwent standard diagnostic angiography to assess all treated vessels, the arteries were specifically identified according to anatomical landmarks that were noted during procedure day and TICI scoring was attributed for the evaluation. Blood was collected, for CBC and bio chemistry. Blood collection, from the animal, was performed after sedation and prior to anesthesia and induction or euthanasia. Animal euthanasia was performed by IV bolus injection of an over dose of potassium chloride (ad effect) while the animal was under general anesthesia.

Harvesting: Detection of instrumented segments was based on the registration performed based on pre-selected anatomical landmarks and hardcopies of angiograms. The instrumented arterial segments were harvested. Harvesting of two native untreated segments was performed for comparative purposes from 2 animals. The harvested segments were kept in a Formalin solution for further histological assessment.

Histological analysis: The samples were prepared by paraffin embedding followed by H&E staining of selected sections. The samples were then submitted for histological evaluation.

In all procedure carried out with the device of this disclosure, no angiographic evidence of arterial wall injury such as dissection, perforation or thrombus formation was observed. TICI-3 score was recorded in 6/6 (100%) vessels, following three attempts in each vessel.

Vasospasm can normally occurs in endovascular procedures during guiding catheter, wire and microcatheter manipulation and device retrieval. In fact, the swine model is much more prone to vasospasm compared with humans. Vasospasm is usually self-limited, and at follow up angiography after 1 hour vasospasm usually resolves. During the procedures only 2/6 simulated attempts (first attempts in each vessel) resulted in vasospasm.

Histological evaluation of the treated arteries at 30 days post procedure and revealed no significant histological findings. Mild endothelial erosions were noted during the follow-up angiography at 30 day, and are considered acute in nature and related to wire or catheter passage. Such findings are within the limits of similar endovascular procedures [10,11].

The invention claimed is:

1. A medical system for anchoring into at least one corpus located in a tubular organ, the system comprising a handling and manipulation apparatus (HMA) and a corpus anchoring unit operable thereby, the HMA being configured for manipulating the corpus anchoring unit into engagement with said corpus;

the corpus anchoring unit comprising:
a deployment wire defining a proximal-distal axis,
at least two generally cylindrical elongated bodies that are spaced apart along said deployment wire, each of said bodies having a proximal end and a distal end and being constituted by at least one wound coiled thread in its deployment state, each of said bodies having a fixed end at either the proximal or distal end and having a free, opposite end that is configured for deploying into at least one deployed state in which each of the threads unwinds in the general radial direction while tracing, during deployment, a generally helical path, and
at least two axially displaceable tip tools, each mounted onto the deployment wire and associated with a respective free end of each of the bodies such that axial displacement of each tip forces at least one respective wound coiled thread to unwind into the at least one deployed state; and
the threads of consecutive bodies along the proximal-distal axis are coiled to permit their helical unwinding movement in respective opposite rotational directions upon axial displacement of their corresponding tip tools;
the HMA being configured to axially displace the deployment wire.

2. The system of claim 1, wherein each of said bodies being configured to unwind at a force applied thereto upon axial displacement of each respective tip tool, which may be the same or different than that applied onto other bodies.

3. The system of claim 1, wherein said bodies are arranged such that (i) odd bodies having free ends at respective distal ends, while even bodies having free ends at respective proximal ends, or (ii) odd bodies having free ends at respective proximal ends, while even bodies having free ends at respective distal ends.

4. The system of claim 1, wherein (i) bodies having a distal free end are fixed to said deployment wire and bodies having a proximal free end are floating, or (ii) bodies having a proximal free end are fixed to said deployment wire and bodies having a distal free end are floating; optionally wherein fixed bodies are associated with floating tip tools, and floating bodies are associated with fixed tip tools.

5. The system of claim 1, wherein each respective tip tool is configured to simultaneously unwind all of the wound coiled threads in its associated body.

6. The system of claim 1, wherein said wound coiled threads are made of a shape-memory metal or alloy.

7. The system of claim 1, wherein the threads are dimensioned to exert a radial force of no more than 1 N (in a conduit having a diameter of 2 mm) on an internal surface of the tubular anatomical organ.

8. The system of claim 1, further comprising at least one closed tube.

9. The system of claim 1, wherein each respective tip tool has an ellipsoid shape, such that the longitudinal axis of each tip tool coincides with the deployment wire, and wherein the maximal diameter of each tip tool is larger than the internal diameter of the associated body.

10. The system of claim 9, wherein each tip tool comprises a tubular element associated with one of the tip tool's proximal or distal ends.

11. The system of claim 10, wherein (i) when a tip tool of the at least two tip tools is associated with a proximal end of a corresponding body, the tubular element is at a proximal end of the tip tool, or (ii) when a tip tool of the at least two tip tools is associated with a distal end of a corresponding body, the tubular element is at a distal end of the tip tool.

12. The system of claim 1, wherein at least one of the tip tools comprises a radiopaque marker.

13. The system of claim 1, wherein the external surface of at least one of the bodies is enveloped by a polymeric layer along a portion of the body's length for limiting the extent of unwinding of the coiled threads.

14. The system of claim 1, further comprising at least one embolic protection element.

15. The system of claim 1, wherein the tubular organ is selected from a blood vessel, fallopian tubes, urinary tract, ureter, urethra, biliary tract, bile ducts, gastrointestinal tract, airways and any other anatomical lumen.

16. A kit for assembly of the system of claim 1, the kit comprising
a handling and manipulation apparatus (HMA),
at least one deployment wire;
a plurality of generally cylindrical elongated bodies, each body being constituted by at least one shape-memory metal or alloy wound coiled thread; and
a plurality of tip tools; optionally comprising a plurality of spacers and/or an embolic protection element.

17. The kit of claim 16, further comprising means for associating the deployment wire with (i) the HMA, (ii) the bodies, and/or (iii) the tip tools.

18. A method for removal of a corpus located in a tubular anatomical organ, comprising:
(a) manipulating a corpus anchoring unit by a handling and manipulation apparatus (HMA) associated therewith, such that the corpus anchoring unit is brought into proximity with the corpus, the corpus anchoring unit comprising:
a deployment wire defining a proximal-distal axis;
at least two generally cylindrical elongated bodies that are spaced apart along said deployment wire, each body having a proximal end and a distal end and being constituted by at least one wound coiled thread in a deployment state, each of said bodies having a fixed end at either the proximal or distal end and having a free, opposite end that is configured for deploying into at least one deployed state in which each of the threads unwinds in the general radial direction while tracing, during deployment, a generally helical path and
at least two axially displaceable tip tools, each mounted onto the deployment wire and associated with the free end of the bodies,
the threads of consecutive bodies along the proximal-distal axis are coiled to permit their helical unwinding movement in respective opposite rotational directions upon axial displacement of their corresponding tip tools;
(b) axially displacing the deployment wire to axially displace at least one tip tool, thereby unwinding at least one coiled thread from its associated body from the deployment state to said at least one deployed state, thereby anchoring the unwound coiled thread into the corpus; and
(c) removing the anchored corpus from the organ by manipulating the corpus anchoring unit out of the organ.

19. The method of claim 18, wherein each of said bodies being configured to unwind at a force applied thereto upon axial displacement of its respective tip tool, which may be the same or different than that applied onto other bodies.

20. A medical system for anchoring into at least one corpus located in tubular organ, the system comprising a handling and manipulation apparatus (HMA) and a corpus anchoring unit operable thereby, the HMA being configured for manipulating the corpus anchoring unit into engagement with said corpus;

the corpus anchoring unit comprising:

a deployment wire defining a proximal-distal axis, at least two generally cylindrical elongated bodies that are spaced apart along said deployment wire, each of said bodies having a proximal end and a distal end and being constituted by at least one wound coiled thread in its deployment state, each of said bodies having a fixed end at either the proximal or distal end and having a free, opposite end that is configured for deploying into at least one deployed state in which each of the threads unwinds in the general radial direction while tracing, during deployment, a generally helical path, and at least two axially displaceable tip tools, each mounted onto the deployment wire and associated with a respective free end of each of the bodies such that axial displacement of each tip forces at least one respective wound coiled thread to unwind into the at least one deployed state; and (i) bodies having a distal free end are fixed to said deployment wire and bodies having a proximal free end are floating, or (ii) bodies having a proximal free end are fixed to said deployment wire and bodies having a distal free end are floating;

the HMA being configured to axially displace the deployment wire.

* * * * *